United States Patent
Sun et al.

(10) Patent No.: US 8,969,090 B2
(45) Date of Patent: Mar. 3, 2015

(54) DNA SEQUENCING METHODS AND DETECTORS AND SYSTEMS FOR CARRYING OUT THE SAME

(75) Inventors: Hongye Sun, Belmont, CA (US); Eric S. Nordman, Palo Alto, CA (US); Mark F. Oldham, Emerald Hills, CA (US); John R. O'Neill, San Bruno, CA (US); Charles Connell, Redwood City, CA (US); Umberto Ulmanella, Foster City, CA (US); Aldrich N. K. Lau, Palo Alto, CA (US); Theofilos Kotseroglou, Hillsborough, CA (US); Kenneth J. Livak, San Jose, CA (US)

(73) Assignee: Life Technologies Corporation, Carlsbad, CA (US)

( * ) Notice: Subject to any disclaimer, the term of this patent is extended or adjusted under 35 U.S.C. 154(b) by 946 days.

(21) Appl. No.: 12/984,269

(22) Filed: Jan. 4, 2011

(65) Prior Publication Data
US 2011/0236984 A1 Sep. 29, 2011

Related U.S. Application Data

(60) Provisional application No. 61/291,950, filed on Jan. 4, 2010, provisional application No. 61/291,953, filed on Jan. 4, 2010, provisional application No. 61/291,964, filed on Jan. 4, 2010, provisional application No. 61/292,061, filed on Jan. 4, 2010.

(51) Int. Cl.
*G01N 27/447* (2006.01)
*G01N 33/543* (2006.01)
(Continued)

(52) U.S. Cl.
CPC .......... *G01N 33/5438* (2013.01); *C12Q 1/6869* (2013.01); *G01N 27/414* (2013.01); *B01L 3/502761* (2013.01); *Y10S 977/924* (2013.01)
USPC ............. 436/94; 977/924; 204/601; 204/451; 521/154

(58) Field of Classification Search
USPC ..................... 436/94; 977/924; 204/451, 601; 521/154
See application file for complete search history.

(56) References Cited

U.S. PATENT DOCUMENTS

2006/0084128 A1 4/2006 Sun
2006/0246497 A1* 11/2006 Huang et al. ...................... 435/6
(Continued)

FOREIGN PATENT DOCUMENTS

WO 2010/138136 12/2010
WO WO-2011/082419 7/2011

OTHER PUBLICATIONS

Shin, Kyeong-Sik et al., Novel T-Channel Nanowire FET with Built in Signal Amplification for pH sensing.(pp. 1-4) 2009. Department of Electrical Engineering, University of California.*
(Continued)

*Primary Examiner* — Rebecca M Fritchman

(57) ABSTRACT

In some embodiments, an analyte detection system is provided that includes a nanochannel, an electrode arrangement, and a plurality of nanoFET devices disposed in the nanochannel. A plurality of nucleic acid base detection components can be used that include a plurality of nanopores, a plurality of nanochannels, a plurality of hybridization probes, combinations thereof, and the like. According to other embodiments of the present teachings, different coded molecules are hybridized to a target DNA molecule and used to detect the presence of various sequences along the target molecule. A kit including mixtures of coded molecules is also provided. In some embodiments, devices including nanochannels, nanopores, and the like, are used for manipulating movement of DNA molecules, for example, in preparation for a DNA sequencing detection. Nanopore structures and methods of making the same are also provided as are methods of nucleic acid sequencing using the nanopore structures. Surface-modified nanopores are provided as are methods of making them. In some embodiments, surfaced-modified nanopores for slowing the translocation of single stranded DNA (ssDNA) through the nanopore are provided, as are nanopores configured to detect each of a plurality of different bases on an ssDNA strand.

5 Claims, 30 Drawing Sheets

(51) Int. Cl.
  *C12Q 1/68* (2006.01)
  *G01N 27/414* (2006.01)
  *G01Q 60/24* (2010.01)
  *C08G 69/42* (2006.01)
  *B01L 3/00* (2006.01)

(56) References Cited

U.S. PATENT DOCUMENTS

| | | | |
|---|---|---|---|
| 2007/0190543 A1 | 8/2007 | Livak | |
| 2007/0238186 A1* | 10/2007 | Sun et al. | 436/94 |
| 2008/0050752 A1 | 2/2008 | Sun et al. | |
| 2008/0084128 A1 | 4/2008 | Neet et al. | |
| 2008/0187915 A1 | 8/2008 | Polonsky et al. | |
| 2009/0181381 A1 | 7/2009 | Oldham et al. | |
| 2009/0226927 A1 | 9/2009 | Sun et al. | |
| 2009/0255801 A1* | 10/2009 | Haas | 204/164 |

OTHER PUBLICATIONS

Maki, W et al., "Nanowire-transistor based ultra-sensitive DNA methylation detection", *Biosensors & Bioelectronics*, 23, 2008, pp. 780-787.

Maki, W et al. "Universal bio-molecular signal transduction-based nano-electronic bio-detection system", *Sensors and Actuators B: Chemical*, 133, 2008, pp. 547-554.

PCT/US2011/020117 International Search Report Mailed Dec. 19, 2011.

PCT/US2011/020117 Written Opinion Mailed Dec. 19, 2011.

EP11728563.5, "European Extended Search Report", May 23, 2013, 6 pages.

PCT/US2011/020117, "International Preliminary Report on Patentability", Jul. 4, 2012, 6 pages.

Li et al., DNA molecules and configurations in a solid-state nanopore microscope, Nature Materials, Sep. 2003, pp. 611-615, vol. 2.

Eid et al., Real-Time DNA Sequencing from Single Polymerase Molecules, Sciencexpress/www.sciencexpress.org, Nov. 20, 2008, 10 pages, 10.1126/science.1162986.

Strukov et al., The missing memristor found, NATURE (Letters), May 1, 2008, pp. 80-83, vol. 453, doi:10.1038/nature06932, Nature Publishing Group.

Williams, How We Found Missing Memristor, Sponsored by Spectrum, published prior to Jan. 4, 2010.

* cited by examiner

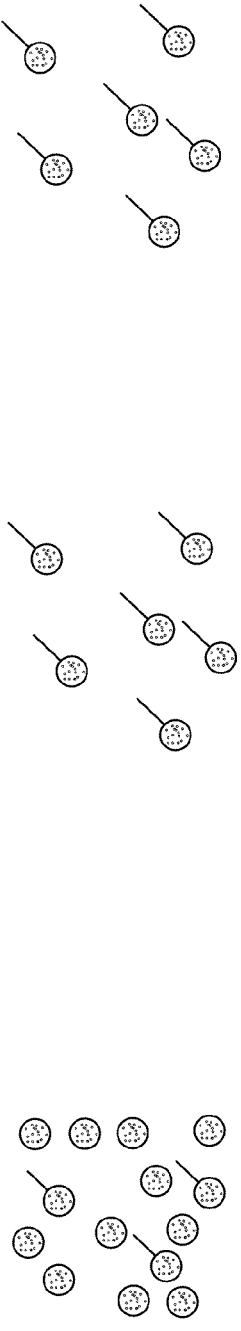

1. Add occasional attachment sites to beads. Most have 0 sites, some have 1 site, few have >1 site. Sites can comprise universal primers, DNA, PNA, Locked DNA, Biotin, and the like.

2. Sort bead to enrich those beads with an attachment site. Can use fluorescent cell sorters, binding to solid supports, and the like, for enrichment.

3. In some embodiments, multiple exonuclease enzymes can be attached to tethers on the beads. This ensures that the enzyme will not be washed away or electrophoresed away.

Exonucleases are not shown, for clarity

FIG. 3A

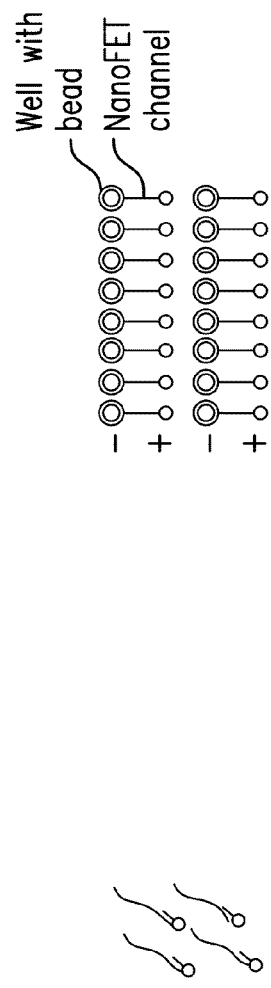

4. Hybridize target DNA to beads. Suppress exonuclease activity until desired time, for example, using temperature, buffer, and the like.

The DNA and attachment size is exaggerated in this diagram

5. Add beads to nanoFET chip Cavities sized to hold single beads with template. Electrodes are shown here.

6. Enable exonucleases and read the sequence.

7. Once the templates are depleted, the beads can be expelled and fresh beads can be added.

FIG. 3B

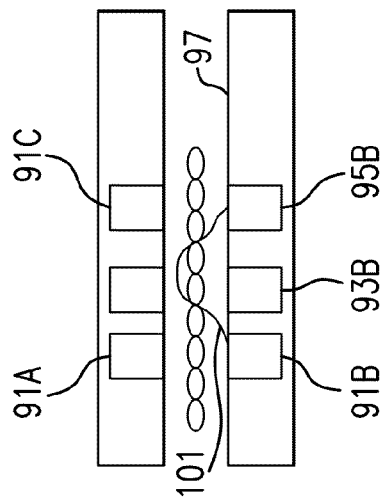
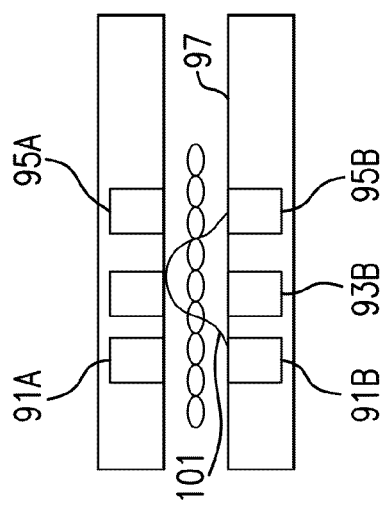
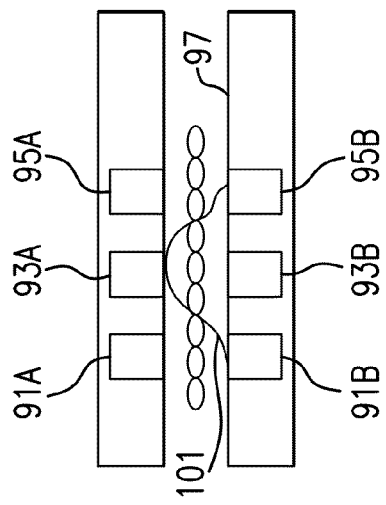

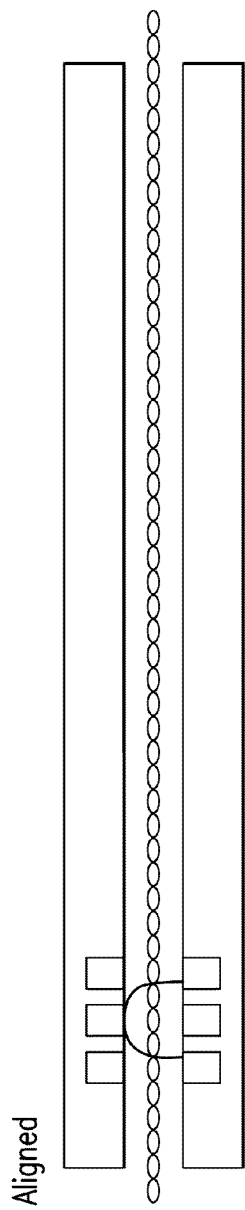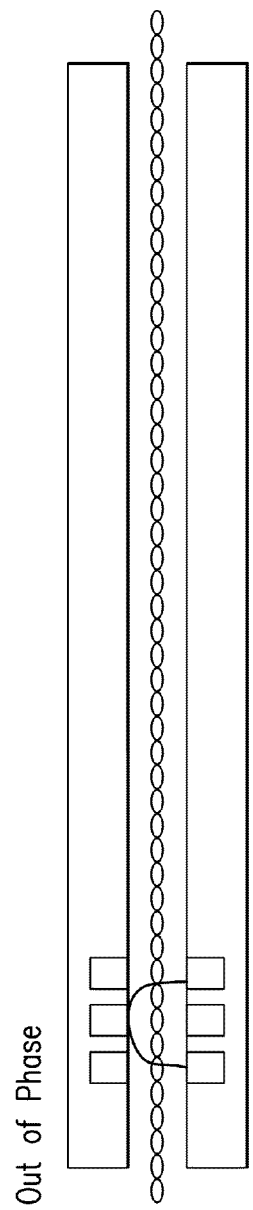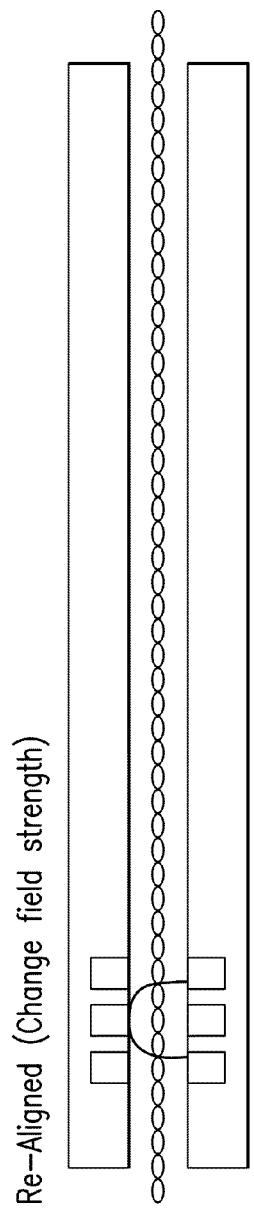

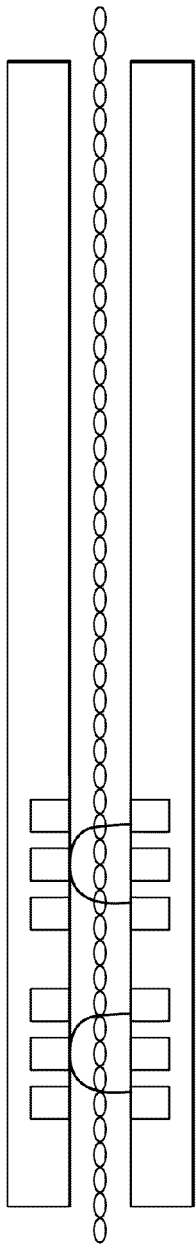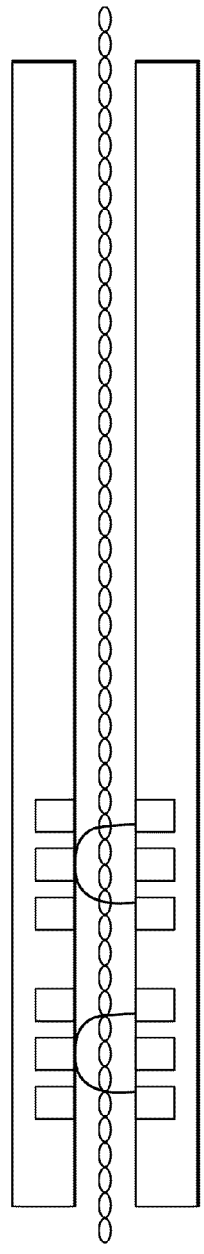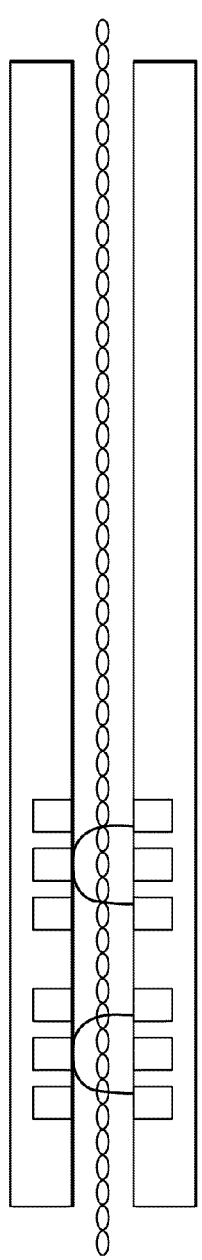
FIG. 8A
FIG. 8B
FIG. 8C

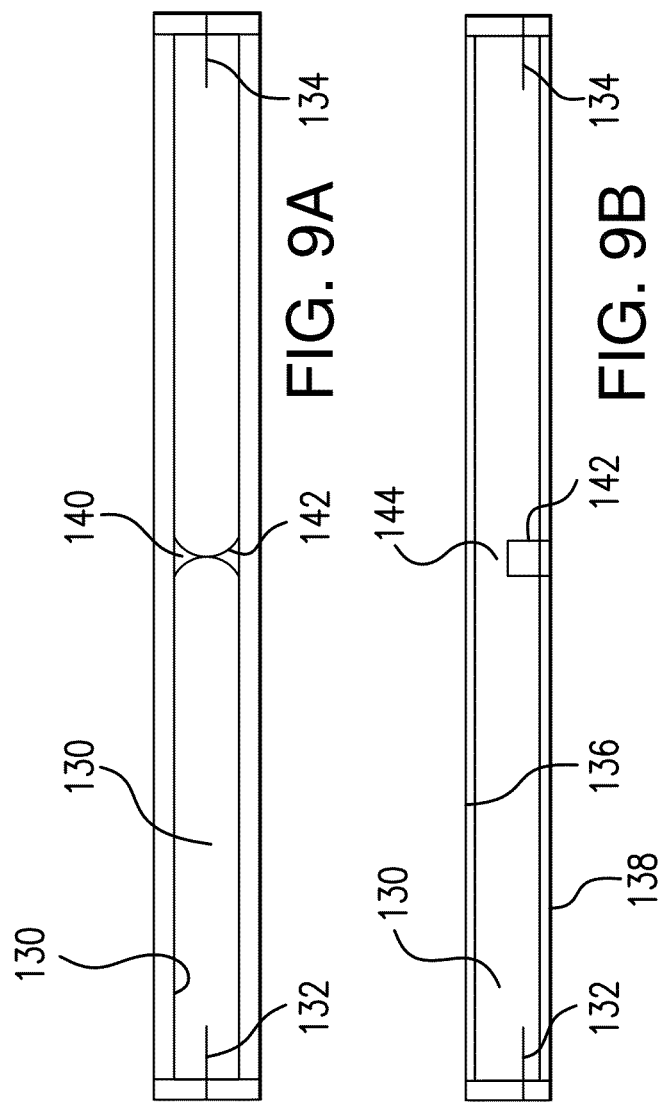

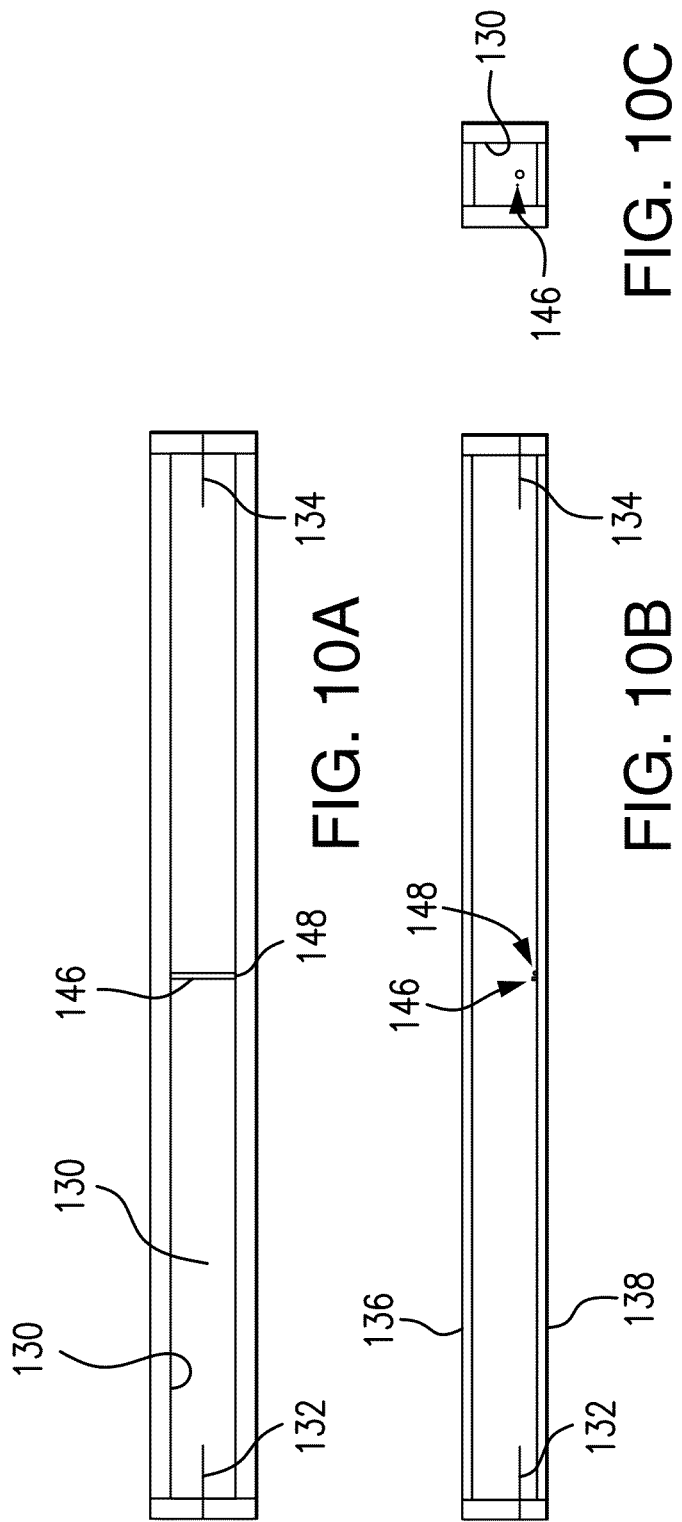

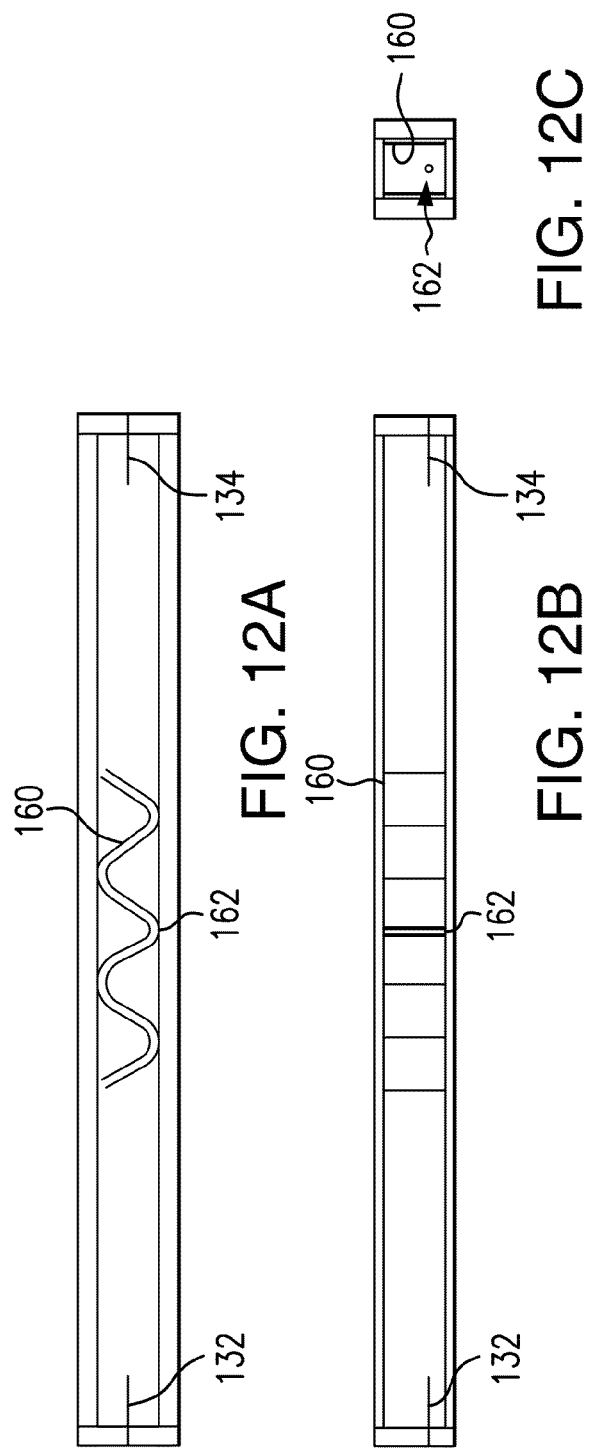

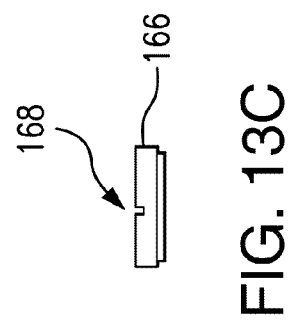
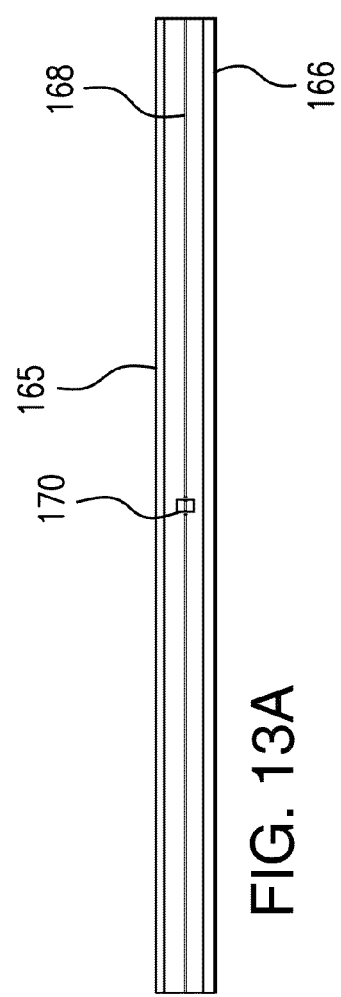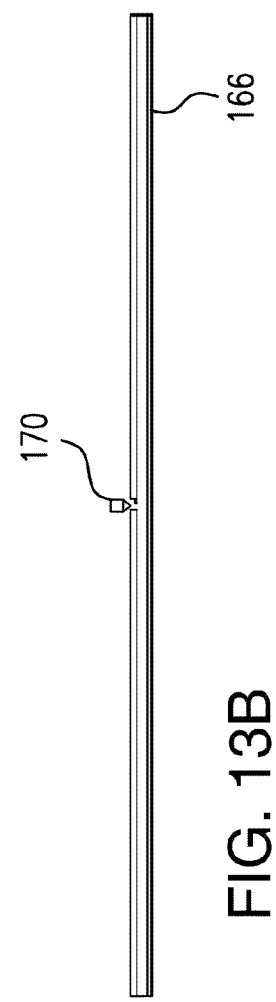

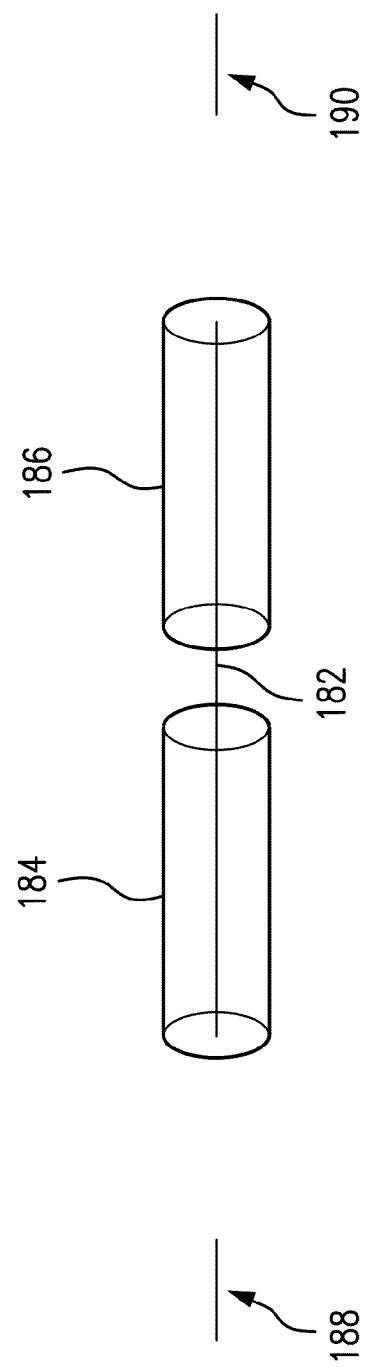

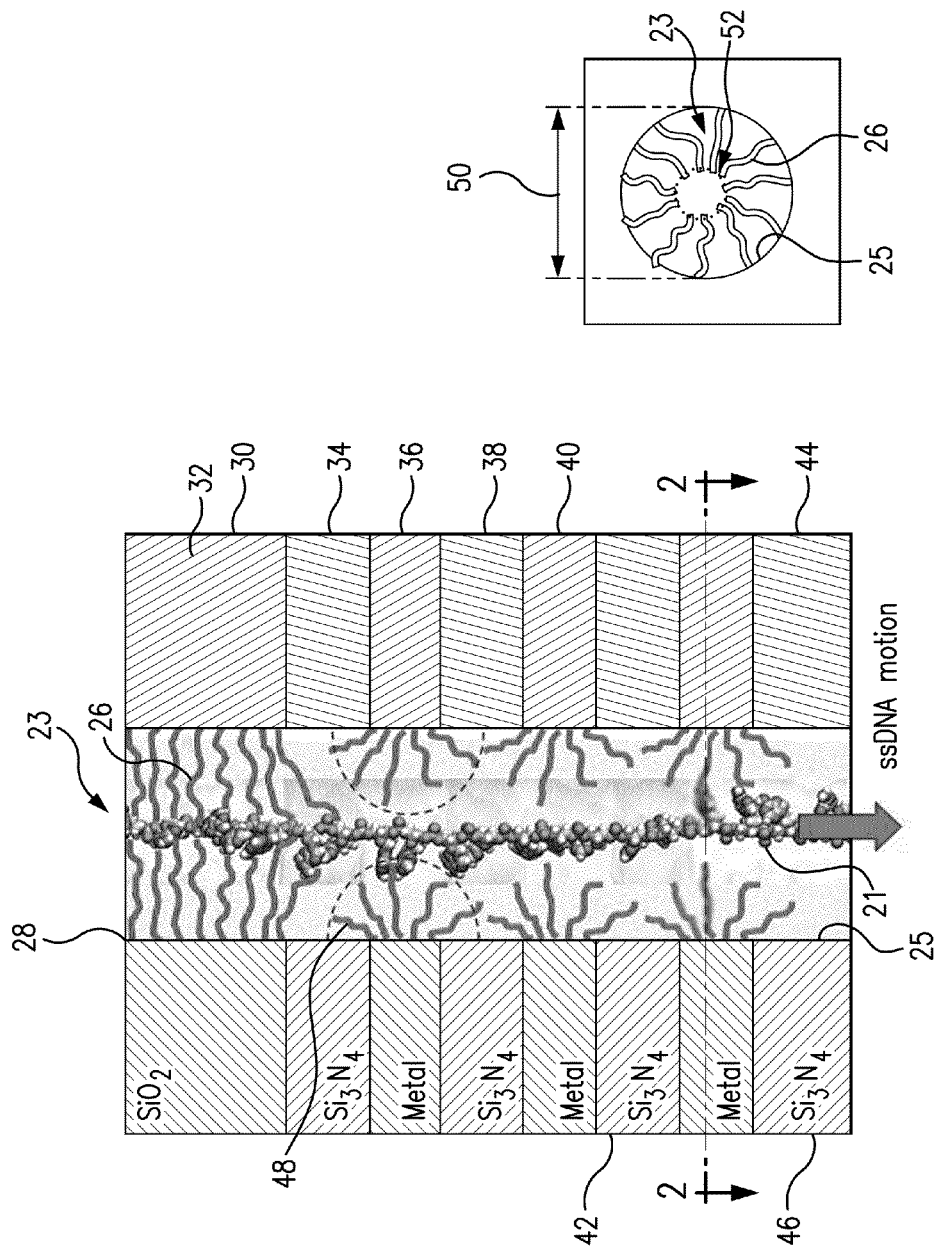

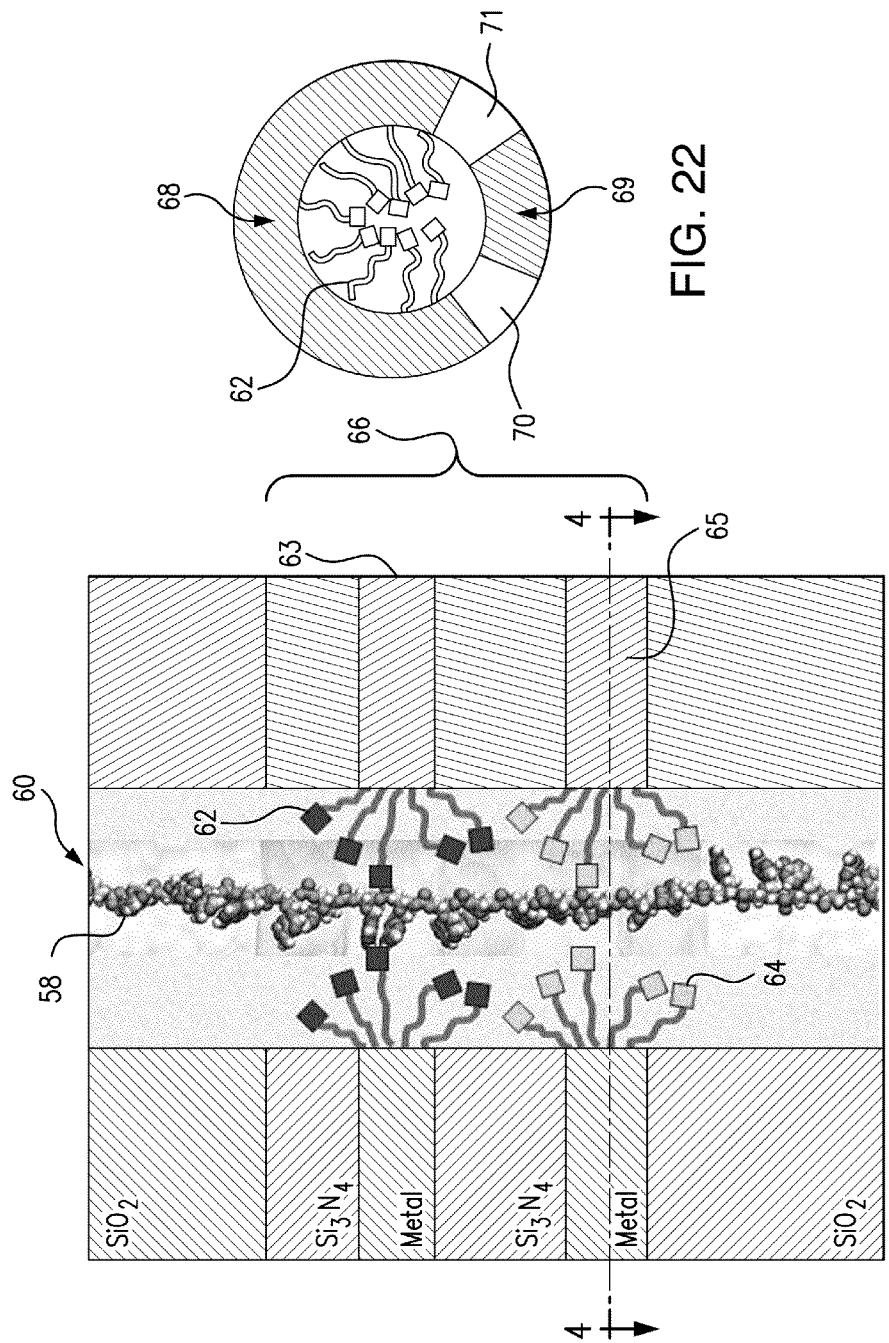

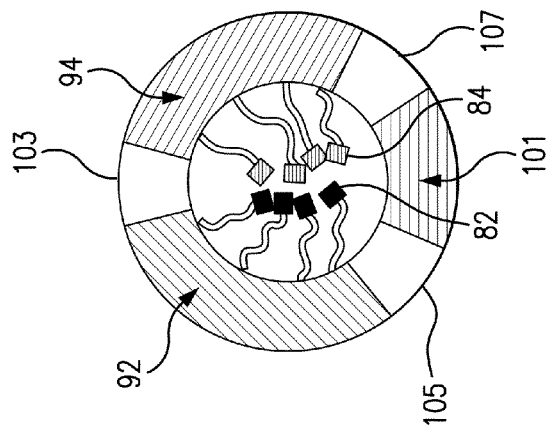
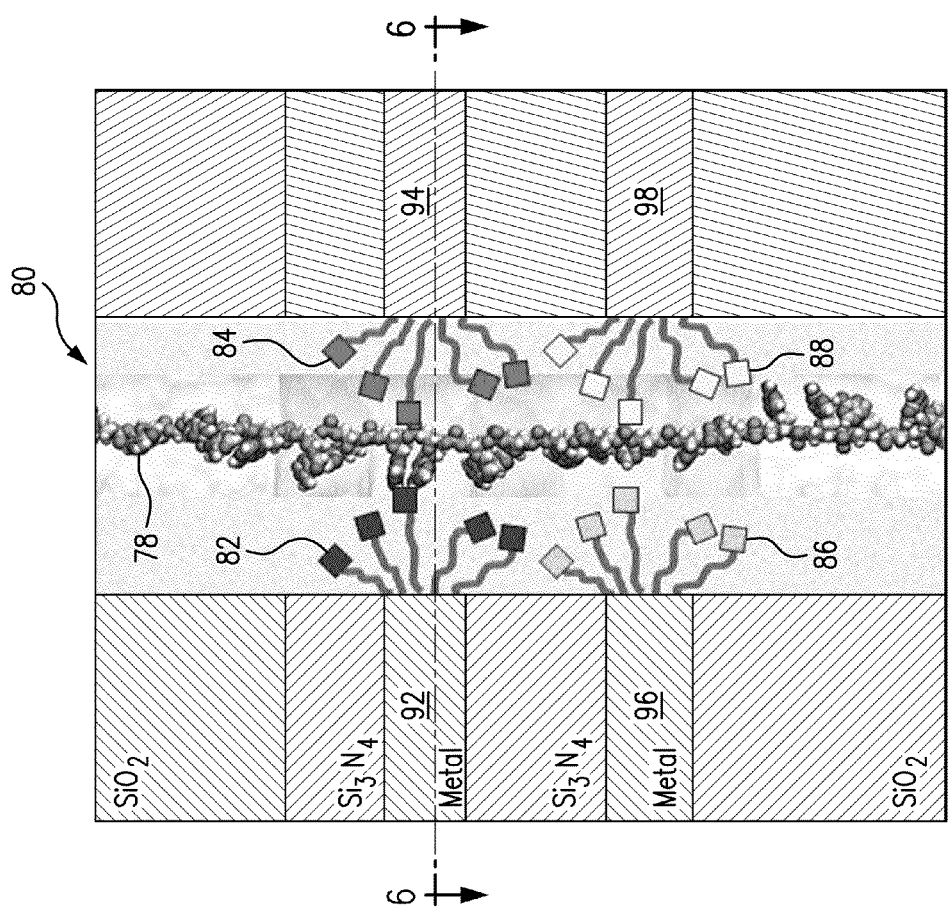
FIG. 24
FIG. 23

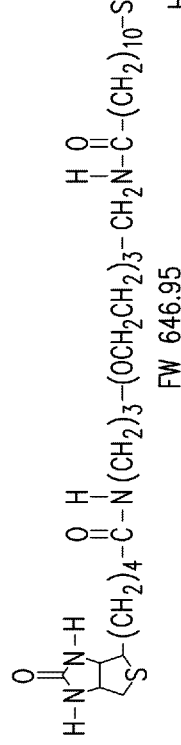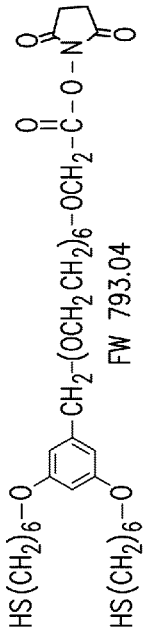

Adenine (Ade)

Guanine (Gua)

Thynine (Thy)

Cytosine (Cyt)

DNA SEQUENCING METHODS AND DETECTORS AND SYSTEMS FOR CARRYING OUT THE SAME

CROSS-REFERENCE TO RELATED APPLICATIONS

The present application claims the priority benefit of earlier filed U.S. Provisional Patent Applications Nos. 61/291,950, 61/291,953, 61/291,964, and 61/292,061, all filed Jan. 4, 2010, and each of which is incorporated herein in its entirety by reference.

FIELD

The present teachings relate to the field of DNA sequencing and detectors useful for DNA sequencing. The present teachings also relate to the field of manipulating movement of DNA and other charged polymers, and systems for carrying out such movement. In addition, the present teachings relate to the field of DNA detection using nanopores.

BACKGROUND

DNA sequencing genetic analysis methods have been complex, expensive, and lengthy. Detectors for carrying out DNA sequencing have been expensive and required optical components. Methods of sequencing nucleic acids have required many copies of a target nucleic acid strand to be sequenced. A need exists for a less expensive, less time-consuming DNA sequencing method and for a less-expensive detector that does not require labeling of the DNA. A need also exists for a less complicated, less expensive DNA manipulation method and system and for a method and system for manipulating DNA molecules to achieve DNA sequencing. Moreover, a need exists for a nucleic acid sequencing method and system that is faster and that does not require substantial amplification of a target strand to be analyzed.

SUMMARY

According to various embodiments, an analyte detection system is provided that comprises a nanochannel having a first end, a second end opposite the first end, a top, and a bottom opposite the top. A pair of electrophoretic electrodes can be provided to move charged analytes through the nanochannel. The electrophoretic electrodes can comprise a first electrophoretic electrode at the first end and a second electrophoretic electrode at the second end. A pair of orthogonal electrodes can also be provided, comprising a first orthogonal electrode at the top and a second orthogonal electrode at the bottom or alternately a first orthogonal electrode on one side and a second orthogonal electrode on the other side. A further pair of orthogonal electrodes can be provided in the axis not utilized by the two previous pairs of electrodes. Yet another option is to have the second and third electrode pairs in the same plane. In some embodiments, the detector can comprise, disposed in the nanochannel, a plurality of nano-field effect transistor devices (nanoFETs). In some embodiments, one or more of the nanoFETs can comprise a vertical FET, for example, an FET arranged vertically and/or comprising a q-tip shape comprising a gold-aluminum alloy tip, on a germanium layer, on a silicon post. The plurality of nanoFETs can comprise at least four different nanoFETs each functionalized with a different receptor analyte than the others. In some embodiments, a target DNA molecule can be bound to a bead and the bead can be disposed in the nanochannel to hold the target molecule during a sequencing method. In some embodiments, an exonuclease enzyme can be bound to a bead and the bead can be disposed in the nanochannel.

According to various embodiments, a DNA sequencing system is provided that comprises a plurality of nucleic acid base detection components and a memristor network. The memristor network can be in electrical communication with the plurality of detectors, and can comprise a 3-dimensional network in some embodiments. The plurality of nucleic acid base detection components can comprise a plurality of nanopores, a plurality of nanochannels, a plurality of hybridization probes, combinations thereof, and the like. In some embodiments, the plurality nucleic acid base detection components comprises at least four detectors, and the four detectors can comprise a first detector configured to detect adenine, a second detector configured to detect cytosine, a third detector configured to detect guanine, and a fourth detector configured to detect thymine. In some embodiments, an additional detector, or one of the four detectors can be configured to detect uracil. In other embodiments, an additional detector or detectors, or one of the four detectors can be configured to detect other nucleosides such as inosine, or pseudouridine. In some embodiments, the detectors may be configured to detect any natural or synthetic nucleic acid analog. In some embodiments, the detectors can be configured to detect proteins, RNA, carbohydrates, other biomolecules, or other molecules used as markers or labels, where the protein, carbohydrate, other biomolecules, or other molecule used as a marker or label is hybridized to, bound to or associated with a portion of a single stranded or double stranded nucleic acid molecule. In some embodiments, the memristor network can comprise a memristor/transistor hybrid network. In some embodiments, memristors and/or memristor hybrid circuits perform real-time data analysis for multiple sensors at nanopore or nanochannel detection sites in a DNA sequencing system.

According to various embodiments of the present teachings, hybridizable oligonucleotides, also referred to herein as coded molecules, can be hybridized to a target DNA molecule and used to detect the presence of various sequences along the target molecule. For example, a target ssDNA molecule can be contacted with a mixture of different coded molecules and the reaction product can be detected using a nanopore, a nanochannel, a combination thereof, or the like. The hybridizable coded molecules can be selected and/or configured to affect ion current travel through a detector, for example, through an electrode pair pathway in a nanopore detector. Each coded molecule that hybridizes can cause a electrical signal through an electrical pathway, which signal can be detected and used to reveal information about the target. Information gathered from the signals detected can be used to determine portions of the sequence of the target and the positions of those portions along the length of the target. In some embodiments, the signals associated with each coded molecule may be unique, allowing direct identification of the coded molecule. In other embodiments, there may be a pattern in the electrical signal generated by coded molecules. The pattern may result from different signals from different detectors, different signal levels from the same detector, from detection from one or more detectors determining that a coded molecule is not proximate to the detector, or interacting with the detector or any combination thereof. A kit comprising mixtures of coded molecules is also provided according to various embodiments of the present teachings, as are methods of genotyping using the kit. The kit can comprise the coded molecules contained together or separately. The kit can also contain one or more standards, reagents, buffers, combinations thereof, and the like.

According to various embodiments, the present teachings provide methods of DNA sequencing and genotyping using the DNA sequencing systems described herein.

According to yet another aspect of the present teachings, devices, systems, and methods of manipulating a DNA molecule or other charged polymers are provided. In some embodiments, DNA can be manipulated for positioning with respect to detectors, to enable DNA sequencing of the polymer. In some embodiments, devices for orienting DNA molecules are provided that comprise a nanopore or nanochannel.

According to various embodiments, a DNA molecule movement device is provided that comprises a nanochannel having a first end, a second end opposite the first end, a top, and a bottom opposite the top. A pair of translation electrodes is also provided, comprising a first translation electrode at the first end of the nanochannel and a second translation electrode at the second end. At least three pairs of orthogonal electrodes are provided, each pair comprising a first orthogonal electrode at the top and a second orthogonal electrode at the bottom. A control unit can be provided for individually controlling the voltage applied to at least one electrode of each electrode pair. In some embodiments, the nanochannel is filled with an electrophoretic medium and the pair of translation electrodes can comprise a pair of electrophoretic electrodes.

According to various embodiments, the present teachings provide methods of DNA sequencing and genotyping using the DNA sequencing systems described herein.

According to various embodiments, DNA molecule manipulation systems are provided for DNA sequencing. The systems can be useful for controlling the movement and velocity of a DNA molecule during a sequencing method. In some embodiments, a DNA manipulation system is provided that comprises a nanochannel having a first end, a second end opposite the first end, a top, and a bottom opposite the top. A pair of electrophoretic electrodes can be provided to move charged analytes through the nanochannel. The electrophoretic electrodes can comprise a first electrophoretic electrode at the first end and a second electrophoretic electrode at the second end. A pair of orthogonal electrodes can also be provided, comprising a first orthogonal electrode at the top and a second orthogonal electrode at the bottom. In some embodiments, the system can comprise, disposed in the nanochannel, a plurality of nano-field effect transistor devices (nanoFETs). The plurality of nanoFETs can comprise at least four different nanoFETs each functionalized with a different receptor analyte than the others. In some embodiments, a target DNA molecule can be bound to a bead and the bead can be disposed in the nanochannel to hold the target molecule during a sequencing method. In some embodiments, an exonuclease enzyme can be bound to a bead and the bead can be disposed in the nanochannel.

According to various embodiments of the present teachings, a DNA molecule manipulation device is provided that uses tunneling current as a detectable signal for determining individual nucleic acid bases of a DNA molecule. The devices can comprise built in redundancy features so bases can be read multiple times. In some embodiments, multiple electrode structures are provided and in some embodiments the DNA is moved with respect to the same electrode several times. In some embodiments, DNA is moved using an electric field or other means, and then held in place utilizing an orthogonal electric field.

According to various embodiments, the DNA strand is stretched using a bond or other mechanism at one or both ends of the DNA molecule, and then a scan head is moved with respect to the bound DNA. In some embodiments, DNA is bound to a surface of a rigid structure on the scale of the DNA strand, for example, bound to a nanotube or nanobead, and then moved together with the structure past a fixed scan head using a nanopositioning stage. In some embodiments, a pair or carbon nanotubes are arranged and separated by about the length of a single base, and DNA is caused to move through both of the carbon nanotubes, and the nanotubes are utilized as electrodes. In some embodiments, two nanotubes are oriented at right angles such that a DNA strand is positioned by one nanotube or nanopost and the base specific tunneling current is read by the other nanotube.

According to various embodiments, the present teachings provide methods of DNA sequencing and genotyping using the DNA sequencing systems described herein.

According to yet other various embodiments of the present teachings, nanopores are provided that can be useful for nucleic acid sequencing, as is a method for forming a nanopore structures. The method can comprise treating a nanopore that is formed through a substrate comprising at least one layer of silicon or silica material. The nanopore can comprise an inner sidewall having exposed silanol groups. In an alternative embodiment, a nanochannel may be utilized. The exposed silanol groups can be reacted with a amino-containing compound such as an amino-containing alkoxysilane to convert the silanol groups to amino-containing functional groups. Then, the amino groups can be reacted with the copolymerization product of an acrylic ester of N-hydroxysuccinimide and an acrylamide. The N-hydroxysuccinimide ester of the acrylic acid reacts with the amino group. In some embodiments, the acrylic acid ester of N-hydroxysuccinimide can be replaced with an acrylic acid of pentafluorophenol. The reaction results in covalently bonding of a copolymerized product on the inner sidewall through amidization. The resulting surface treatment polymer can be useful for affecting the translocation rate of a ssDNA molecule through the nanopore, for stretching out the ssDNA as it passes through the nanopore, for imparting a preferential orientation to the ssDNA, to physically confine the ssDNA to a region within the nanopore, to decrease the separation between the sensing element and the ssDNA, to decrease the effective size of the nanopore, thus allowing for larger manufacturing tolerances, a less demanding manufacturing process. Individual bases of the stretched out ssDNA can thus be more readily detected by detection moieties in the nanopore, compared to when detection of the bases in a non-stretched orientation.

According to various embodiments, the term "nanopore" as used herein applies also to the concept of a nanochannel. The term "nanopore" does not include any limitations as for geometry, aspect ratio, size, shape, cross-sectional profile, etc, other that a salient dimension characterizing the geometry of the "nanopore" itself is smaller than 0.1 microns. The nanopore can be "through" or "blind", composed of a single or more materials, arranged e.g. in layers, or others, each layer made of one or more materials. The layer, as thin as a single atom, can be of non-constant thickness and depart from a substantially planar geometry. The electrically conductive material ("electrode") can be flush with respect to the local nanopore sidewall geometry, can protrude toward the central axis of the pore, or can be undercut in the peripheral direction. The electrode layer does not need cover the entire plane, and only a portion of the layer can be exposed inside the nanopore, in some embodiments. Multiple separate electrodes can be located on the same layer and individual portions exposed separately on the surface of the nanopore.

According to various embodiments, a method is provided for surface modification of a nanopore through a substrate that comprises at least one layer of a conductor, which may be a carbon nanotube, graphene layer, InSnO, noble metal or noble metal alloy, used as an electrode layer. The electrode layer can, for example, be electrically connected to a voltage source and an applied potential can be used that causes the electrode to act as an anode. At least a portion of an inner sidewall of the nanopore can be defined by an exposed surface of the at least one layer. In some embodiments, the layer can comprise gold. According to various embodiments, the exposed noble metal or alloy thereof can be reacted, at the exposed surface thereof, with a thiolated compound, for example, α-mercapto-polyol, such that a sulfur linkage to the exposed metal surface is formed. The thiolated compound can also comprise a terminal nucleic acid base affinitive moiety that that can enable a non-covalent, physical, temporary, and reversible affinity. Although binding may be referred to herein in this regard, it is to be understood that the selective association is non-covalent, physical, temporary, and reversible. Herein, "binding" can refer to a "non-zero/positive affinity," the phrase "temporary binding" or can refer to affinity driven interaction or sensing, of which actual binding is only one of the many possible interactions or sensing opportunities. Upon temporarily selectively associating to a complementary nucleic acid base, the association can affect a current or voltage passing through the electrode. The change in current or voltage can then be detected and analyzed to determine what type of base temporarily bound to the binding moiety. Furthermore, a change in electrical signal, for example, a DC signal, an AC signal, or both, can be sensed, which results from a variation of any of a variety of electrically transducatable properties, for example, resistance, capacitance, inductance, polarization moment, tunneling current, and the like.

In some embodiments, a nanopore formed in a substrate is provided wherein the substrate comprises a plurality of spaced apart layers, each comprising a noble metal or noble metal alloy. In some embodiments, at least one of the plurality of layers can comprise an exposed surface that has bonded thereto a first nucleic acid base binding (affinitive) agent. At least one different layer of the plurality of layers can comprise an exposed surface that has bonded thereto a second nucleic acid base binding (affinitive) agent that is different than the first one. Each of the first and second nucleic acid base binding (affinitive) agents can comprise, for example, a thiolated glycol comprising at least one deoxyribonucleotide phosphate. The nanopore structure can be configured such that when the first or second nucleic acid base binding (affinitive) agent temporarily associates to a complementary base of an ssDNA molecule passing through the nanopore, a change in current, voltage, or both, through the respective electrode, can be detected and used to identify the base temporarily bound.

According to various embodiments, a method is provided that comprises forming a nanopore through a substrate that comprises at least one layer of graphene. The nanopore can comprise an inner sidewall, at least a portion of which comprises an exposed graphene surface. The exposed graphene surface can be modified by a reaction that covalently binds thereto a nucleic acid base binding (affinitive) agent. The binding (affinitive) agent can comprise a carbonyl linkage moiety and a deoxyribonucleotide phosphate. In some embodiments, the phosphate can comprise a diphosphate or a triphosphate. In an alternative embodiment, the binding agent can be attached directly to the graphene, without a linkage group. In a further embodiment, the binding agent can consist of a nucleobase, without the sugar or phosphate groups that are part of a customary dNTP.

According to yet other embodiments of the present teachings, a nanopore formed through a substrate is provided. The nanopore can comprise an inner sidewall and can have a diameter. The inner sidewall can be surface-modified to have chemically bound to the surface thereof a polymer extending radially inwardly, for example, toward the radial center of the nanopore. The polymer can extend inwardly by a distance that is at least 25% of the length of the diameter, for example, about 35% or about 45% of the length of the diameter. The diameter can be 100 nm or less, for example, 20 nm or less, or 10 nm or less. The polymer can comprise any of the nanopore surface-modifying polymers described herein.

In yet other embodiments of the present teachings, a multilayer nanopore is provided, that is formed through a substrate. The nanopore can comprise an inner sidewall defined, at least in part, by a first layer. The first layer can comprise an exposed surface at the inner sidewall. In some embodiments, the exposed surface can define an electrode, one or more counter-electrodes, and one or more dielectrics that separate the electrode from the one or more counter-electrodes. In some embodiments, at least two counter-electrodes are defined at the nanopore inner sidewall and each can be surface-modified with a different nucleic acid base binding (affinitive) agent covalently bonded thereto at the exposed surface. With such a configuration, each of the two different nucleic acid bases can be identified by the first layer electrodes. Configurations having multiple different layers of electrodes can be used to detect all possible nucleic acid bases and/or to provide detection redundancies useful to verify results. These and other aspects of the present teachings will be more fully understood with reference to the accompanying drawings.

BRIEF DESCRIPTION OF THE DRAWINGS

FIGS. 3A-3B schematically illustrate a method of preparing beads, enzymes, and target DNA to be used in a nanoFET chip for DNA sequencing, according to various embodiments of the present teachings.

FIGS. 5A-5C depict a DNA molecule manipulation nanochannel showing three pairs of electrodes, wherein the electric field phase and the DNA spacing is in perfect alignment (FIG. 5A), out of alignment (FIG. 5B), and in tuned alignment (FIG. 5C), according to various embodiments of the present teachings.

FIGS. 6A-6C depict a DNA molecule manipulation nanopore showing three pairs of electrodes, wherein the electric field phase and the DNA spacing is aligned (FIG. 6A), out of phase (FIG. 6B), and re-aligned (FIG. 6C), according to various embodiments of the present teachings.

FIGS. 8A-8C depict a DNA molecule manipulation nanopore two phase device showing three pairs (one set) of electrodes in one layer and three pairs (one set) of electrodes in another layer, wherein the two sets are out of phase with each other (FIG. 8A), the two sets are out of phase with each other (FIG. 8B), and the two sets are re-aligned by a change in field strength (FIG. 8C).

FIGS. 9A-9C are a top view, side view, and end view, respectively, of a DNA molecule manipulation channel showing electrode arrangements and an electrode gap, according to various embodiments of the present teachings.

FIGS. 10A-10C are a top view, side view, and end view, respectively, of a DNA molecule manipulation channel showing electrode arrangements and a tunneling electrode, according to various embodiments of the present teachings.

FIGS. 12A-12C are a top view, side view, and end view, respectively, of a DNA molecule manipulation channel in the form of a serpentine channel, and showing electrode arrangements and tunneling electrodes, according to various embodiments of the present teachings.

FIGS. 13A-13C are a top view, side view, and end view, respectively, of a DNA molecule manipulation binding trough and an atomic force microscope positioned for scanning the trough, according to various embodiments of the present teachings.

FIG. 15 is a side view of a dual-nanotube configuration according to various embodiments of the present teachings, wherein a DNA molecule is stretched through two carbon nanotubes that function as tunneling electrodes, the distance of a single base of DNA separates the nanotubes, and a tunneling current between the tubes is used to characterize the isolated base in the gap.

FIG. 19 is a schematic illustration of a cross-sectional side view of an ssDNA molecule being moved through a nanopore according to various embodiments of the present teachings.

FIG. 20 is a top view of the nanopore shown in FIG. 19, taken through line 2-2 of FIG. 19, and depicting the physical pore diameter and the effective pore diameter.

FIG. 21 is a schematic illustration of a cross-sectional side view of an ssDNA molecule being moved through a nanopore according to various embodiments of the present teachings, wherein the nanopore comprises selective nucleic acid base binding (affinitive) agents bound to surfaces of the electrodes.

FIG. 22 is a top view of the nanopore and molecule shown in FIG. 21, taken through line 4-4 of FIG. 21, showing an electrode and counter-electrode configuration according to various embodiments of the present teachings.

FIG. 23 is a schematic illustration of a cross-sectional side view of an ssDNA molecule being moved through a nanopore according to various embodiments of the present teachings, wherein the nanopore comprises selective nucleic acid base binding (affinitive) agents to bind with the four different nucleic acid bases A, C, G, T, wherein the base binding (affinitive) agents are bound to four different respective electrodes.

FIG. 24 is a top view of the nanopore and molecule shown in FIG. 23, taken through line 6-6 of FIG. 23, showing two electrodes and one counter-electrode in a configuration according to various embodiments of the present teachings.

FIGS. 32A-32F show the chemical structures of six respective thiolated polyols that can be used to conjugate a nucleic acid binding (affinitive) agent on the surface of a gold anode, according to various embodiments of the present teachings.

DETAILED DESCRIPTION

NanoFETs, Nanochannels, and Nanopores

Figure 1:
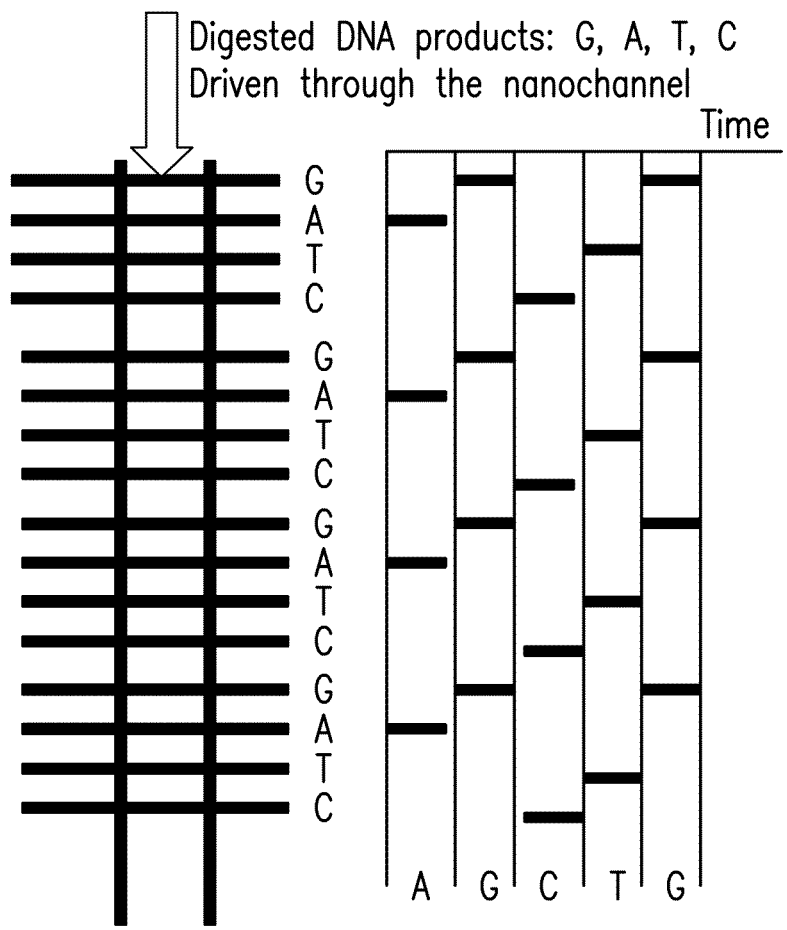
FIG. 1 is a schematic illustration of a detection scheme according to various embodiments of the present teachings wherein DNA Sequencing is carried out using four serial arranged nanoFET stacks, each stack comprising four nanoFETs functionalized with G, A, T, and C receptor molecules, respectively.

According to various embodiments, an analyte detection system is provided that comprises a nanochannel having a first end, a second end opposite the first end, a top, and a bottom opposite the top, or alternately a first orthogonal electrode on one side and a second orthogonal electrode on the other side. A pair of electrophoretic electrodes is provided, comprising a first electrophoretic electrode at the first end and a second electrophoretic electrode at the second end. A pair of orthogonal electrodes is also provided, comprising a first orthogonal electrode at the top and a second orthogonal electrode at the bottom. A further pair of orthogonal electrodes can be provided in the axis not utilized by the two previous pairs of electrodes. Yet another option is to have the second and third electrode pairs in the same plane. Disposed in the nanochannel are a plurality of nano-field effect transistor devices (nanoFETs) disposed in the channel. In some embodiments, one or more of the nanoFETs can comprise a vertical FET, for example, an FET arranged vertically and/or comprising a q-tip shape comprising a gold-aluminum alloy tip, on a germanium layer, on a silicon post. The plurality of nanoFETs can comprise at least four different nanoFETs each functionalized with a different receptor analyte than the others. In some embodiments, a target DNA molecule can be bound to a bead and the bead can be disposed in the nanochannel to hold the target molecule during a sequencing method. In some embodiments, an exonuclease enzyme can be bound to a bead and the bead can be disposed in the nanochannel.

According to various embodiments, a DNA sequencing device is provided that comprises nanoFETs which have been functionalized to detect charge changes on the surfaces of the nanoFETs. The surfaces of the respective nanoFETs can be functionalized with analyte receptor molecules exhibiting higher affinity to the intended analyte than the same nanoFETs would have without the analyte receptor molecules. In some embodiments, the receptor molecules can comprise nucleic acid base binding moieties that can temporarily bind to bases of a target nucleic acid, for example, by hydrogen binding. Other binding moieties can be utilized. Such functionalized nanoFETs can be aligned in a sequential manner in a nanochannel as schematically shown, for example, in FIG. 1. In other embodiments, the detection can result from the interaction of an electric field with molecule that has temporarily bound with the nanoFET. The field can be a DC field, an AC field or a combination of a DC and AC fields. In other embodiments, an electrode in close proximity can functionalized with analyte receptor molecules exhibiting higher affinity to the intended analyte than the same electrode would have without the analyte receptor molecules. In some embodiments, the receptor molecules can comprise nucleic acid base binding moieties that can temporarily bind to bases of a target nucleic acid, for example, by hydrogen binding. Other binding moieties can be utilized. In yet other embodiments, both the nanoFET and the electrode can be functionalized. In some embodiments, the same moiety can be used to functionalize the nanoFET and the electrode. In other embodiments, different moieties can be used to functionalize the nanoFET and the electrode. In some embodiments, an electrode in proximity to a nanoFET can be within 1 m of the nanoFET. In other embodiments, the electrode in proximity to a nanoFET can be from 1 nm to 10 nm from the nanoFET. In yet other embodiments, an electrode in proximity to a nanoFET can be from 10 nm to 100 nm from the nanoFET.

As illustrated in FIG. 1, analytes can be made to migrate through the nanochannel by applying an electric field and temporarily binding the analytes to the functionalized surfaces of the modified nanoFETs. The temporary binding can cause a unique physical signal such as a specific conductance. Other methods of transport can be used and include, for example, fluid flow, centripetal force, combinations thereof, and the like. In some embodiments, a nanoFET A is functionalized with a receptor molecule for A, a nanoFET B is functionalized with a receptor molecule for B, a nanoFET C is functionalized with a receptor molecule for C, and a nanoFET D is functionalized with a receptor molecule for D. A single detection module for A, B, C, and D can be constructed by aligning the A, B, C, and D nanoFETs. In some embodiments, a plurality of detection modules can be serially connected to increase the detection accuracy because the same analyte can be made to bind with multiple nanoFETs multiple times. By using multiple nanoFETs of each type, the analytes can be detected multiple times, increasing sensitivity and accuracy. In some embodiments, different numbers of nanoFETs may be used that are functionalized with different molecules. As a nonlimiting example, if A is more difficult to detect than B, C or D, more nanoFET detectors may be functionalized with A than the number of nanoFET detectors functionalized with B, C or D. Any combination and any order of functionalized detectors may be utilized. In some embodiments, any combination and any order of differently functionalized electrodes that are in proximity to a nanoFET may be utilized. In other embodiments, any combination and order of similarly or differently functionalized electrodes and nanoFETs may be utilized, where each of the electrodes and the nanoFETs that are in respective proximity may be functionalized. In other embodiments, any combination and order of similarly or differently functionalized electrodes and nanoFETs may be utilized, where some of the electrodes and the nanoFETs that are in respective proximity may be functionalized.

The device and method can be used for any analyte detection, for example, by attaching appropriate different receptor molecules. DNA sequencing is used herein to simply exemplify, not limit, the present teachings. In some embodiments, the receptor molecules can comprise bases that are complementary to the analyte bases to be detected, for example, T for A, A for T, C for G, and G for C. In some embodiments, the receptor molecules can comprise synthetic receptors such as PNAs or other non-DNA receptors. In some embodiments, an additional detector, or one of the four detectors can be configured to detect uracil. In other embodiments, an additional detector or detectors, or one of the four detectors can be configured to detect other nucleosides such as inosine, or pseudouridine. In some embodiments, the detectors may be configured to detect any natural or synthetic nucleic acid analog. In some embodiments, the detectors can be configured to detect proteins, RNA, carbohydrates, other biomolecules, or other molecules used as markers or labels, where the protein, carbohydrate, other biomolecules, or other molecule used as a marker or label is hybridized to, bound to or associated with a portion of a single stranded or double stranded nucleic acid molecule. In other embodiments, the analyte detection system can be used to determine the sequence or partial sequence of a protein, by the use of appropriate analyte receptor molecules.

In some embodiments, the nanoFETs can be fabricated using nanowire transistors, carbon tube transistors, graphene transistors, or other more standard semiconductor-based transistors. In some embodiments, additional amplification of the current from the nanoFET can be performed adjacent the nanoFETs to minimize noise. In some embodiments, an amplifier such as a voltage amplifier, a current amplifier, an integrator, a combination thereof, and the like, can be used. In some embodiments, an amplifier that performs additional amplification, which is adjacent to the nanoFET can be made as part of the same set of processes in which the nanochannel and or nanoFET is fabricated. In some embodiments, an amplifier that performs additional amplification, which is adjacent to the nanoFET can be made as part of a different set of processes from those used to fabricate the nanochannel and or nanoFET, but may be still part of the same structure. In other embodiments, the an amplifier that performs additional amplification, which is adjacent to the nanoFET can be made as part of a separate structure. The separate structure can be a printed circuit board, a hybrid circuit.

According to various embodiments, a DNA molecule can be digested sequentially by an exonuclease enzyme to form nucleotide monophosphate products that are negatively charged. In an exemplary embodiment, the products can be introduced into the nanochannel, or to a nanopore, which is embedded with nanoFETs functionalized with receptor molecules for G, A, T, C, and/or other nucleosides. The binding time duration can be tuned by tuning the electric-field strength generated by the electrophoretic electrodes or by tuning the affinities of the receptor molecules immobilized on the nanoFET. Sequence information is the most important information in DNA sequencing, so the binding can be a transitory event, which can be used to prevent phasing errors of the sequence information.

Figure 2:
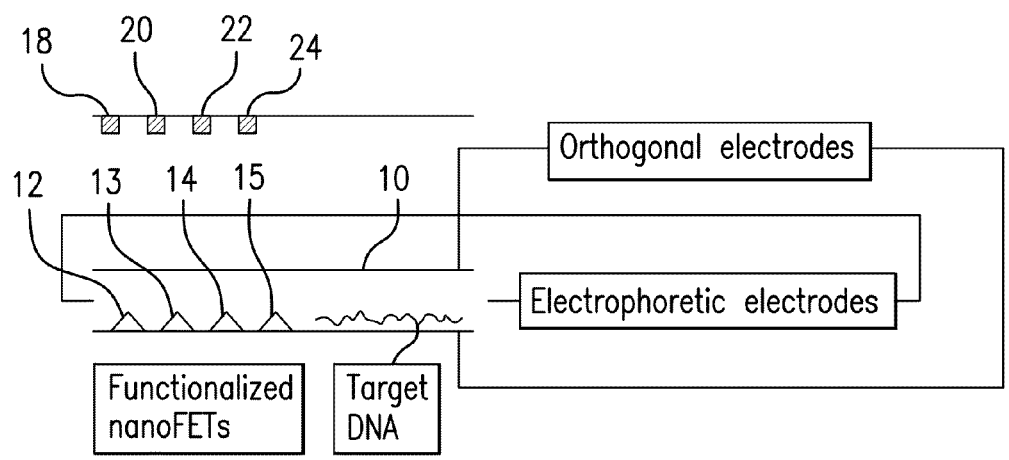
FIG. 2 is a schematic illustration of a detection system according to various embodiments of the present teachings and comprising an electrophoretic channel, a plurality of functionalized nanoFETs arranged in the channel, electrical circuitry, and a DNA target molecule to be sequenced in the nanochannel.

To achieve efficient detection, the nucleotides can be focused on the nanoFET by applying an electric-field in directions other than the flowing direction. FIG. 2 shows an exemplary arrangement wherein orthogonal electrodes are arranged to pull negatively charged product analytes down to the bottom of a nanochannel 10, and electrophoretic electrodes are arranged at opposite ends of nanochannel 10 to move the products through the nanochannel and across four different nanoFETs 12, 13, 14, and 15. NanoFETS 12, 13, 14, and 15 can be functionalized as described herein or with nucleic acid base binding agents comprising nucleic acid bases and linkage moieties, for example, a thiolated diol linkage to a gold anode nanoFET surface. As shown in FIG. 2, counter-electrodes 18, 20, 22, and 24 can be provided to form electrode pairs with nanoFETs 12, 13, 14, and 15, respectively. In some embodiments, this is achieved by creating a very small channel through which the dNTPs can move, for example, channels as small as 5 nm×100 nm. In other embodiments, the width of the nanochannel can be wider than 5 nm, where one of the nanoFET or electrode is configured on one wall of the nanochannel, while the other of the nanoFET or electrode can be configured to be on the tip of an AFM (Atomic Force Microscope). The tip of the AFM can then be configured to be placed within the nanochannel. The tip of the AFM can be configured to be adjustable with respect to the one of the nanoFET or electrode on the wall of the nanochannel. Multiple AFM tips can be used, where a number of the tips can be adjusted together, for example two, four, eight or more tips can be configured to be adjusted together. Alternatively, each of the multiple AFM tips can be individually adjustable. In other embodiments, the nanoFET can be replaced with another electrode, such that the two electrodes can be configured in a pair to measure a tunneling current through the sample molecule. One or both of the tunneling current electrodes can be functionalized with moieties that can interact with the sample molecule. The two electrodes in the pair of tunneling electrodes can be functionalized with the same moiety, or with different moieties on each of the electrodes in the tunneling electrode pair.

In some embodiments, an electric field can be applied orthogonal to the plane in which the nanoFETs are placed to insure that they will interact with the receptor molecules on the nanoFETs. In some embodiments, the field responsible for transporting the dNTPs through the nano-channel can be removed so that there is sufficient time for interaction and measurement. In some embodiments, the orthogonal field can be oscillated, for example, to be synchronous to changes in the electrophoretic field to permit interactions with the affinity molecules attached to the nanoFETs, or tunneling electrodes. In some embodiments, the orthogonal field can be modulated to change the rate of binding or unbinding of the nucleotides. In some embodiments, the orthogonal field can be configured to be at a frequency that is resonant with an oscillation of a portion of the sample molecule. In some embodiments, the frequency of the orthogonal field can be changed over a range, such that a difference in the detected tunneling current or current in the nanoFET can be determined between an intended portion of the sample molecule or analyte which has bound to one of an electrode, tunneling electrode or nanoFET, due to the higher affinity of the receptor associated with the electrode, tunneling electrode, or nanoFET and the intended analyte than for other unintended portions of the sample molecule or analytes. In some embodiments, the difference in detection may result from a change in the amount of tunneling current or current through the nanoFET. In other embodiments, the difference may result in a change in the phase of the tunneling current or current through the nanoFET. In yet other embodiments, the detected difference can result from a combination of the amount and the phase of the tunneling current or current through the nanoFET. Temperature, buffer composition, and the like, can be controlled to provide appropriate binding times. In some embodiments, the temperature can be cycled to provide controlled binding and unbinding. In some embodiments, a second orthogonal pair, or group of electrodes may be used, where the second pair of orthogonal electrodes may be used to position the sample molecules in the axis orthogonal to the electrophoretic electrodes. This second orthogonal pair of electrodes can be used to position the sample molecule. The positioning of the sample molecule or analyte(s) can result in improved opportunity for binding, or interaction between the functionalized electrode, tunneling electrode, or nanoFET than would exist without the presence of the field resulting from the second orthogonal pair or group of electrodes. The improved binding or interaction between the sample molecule or analyte(s) can result in improved detection from the tunneling current or current in the nanoFET.

FIGS. 3A-3B schematically illustrate a method of preparing beads to be used in a nanoFET chip for DNA sequencing, according to various embodiments of the present teachings. The method can be used to prepare beads useful in a device such as the device shown in FIG. 2. As shown in FIGS. 3A-3B multiple exonuclease enzymes can be tethered to beads, a target DNA can be hybridized to an attachment site on the beads, and the beads can be used to hold the target in the device.

As an exemplary nanoFET chip device operates, the exonuclease cleaves dNTPs one at a time from the target DNA and the cleaved dNTPs are caused to move across the functionalized nanoFETs or tunneling electrodes where the dNTPs are detected. In some embodiments, target DNA is prevented from being swept through the nano-channel by binding the target DNA to a substrate. This can be done near an electrode that causes the dNTPs to be swept through the nano-channel, or somewhere between the electrode and the nanoFETs. Depending on the charge of the exonuclease enzyme, it may be necessary to similarly bind it to the substrate through a linker of sufficient length that it can interact with the target DNA. There could be several enzymes in the vicinity of each target DNA in order to minimize time for the enzyme action.

In some embodiments, the voltage associated with sweeping out the released dNTPs into the nanochannel can be removed or modulated in order to permit interaction between the target DNA and the tethered exonuclease enzymes. In some embodiments, other means of changing the speed of the sample molecules can be utilized. This part of the device can be in an area where there is no orthogonal field so as to prevent interaction between the target DNA and the exonuclease. In some embodiments, both the target DNA and the exonuclease enzyme can be removed and replaced. Attachment can be effected by utilizing ligated primers of DNA PNA, or utilizing nonspecific primers. In some embodiments, other methods of attachment such as using Biotin and Streptavidin can be used. In some embodiments, the target DNA can have one strand protected from activity by the exonuclease, such that the second strand can be synthesized by an added polymerase, permitting repeated degradation by an exonuclease enzyme, and subsequent repeated detection of the DNA sequence. The target DNA can have a universal primer ligated onto one end, with subsequent addition of the complement which may be added with the polymerase. Alternatively, the primer may be a hairpin primer, obviating the need for a second primer.

According to various embodiments, the device can have an array of channels to increase throughput. Target DNA can be attached to the substrate in such a way that a single target is associated with each channel; enrichment schemes such as that described in WO 2006/135782 can be used to ensure odds better than would otherwise result from a Poisson distribution, and such reference is incorporated herein in its entirety by reference. The channels can be fabricated in several different ways. In some embodiments, the transistors are fabricated on a planar surface and then a channel structure is created, for example, out of a dielectric material. Polymethylmethacrylate (PMMA) can be used. In some embodiments, the channel is created out of silicon, for example, by etching utilizing natural crystal lines to create a V groove, or utilizing more traditional vertical etching. The fabrication can also comprise metallization, forming implants on the sides of the channel, and the addition of carbon nano-tube or nano-wire detector components. The channels can be physically separated by walls or passively separated by an empty zone akin to having lanes on a gel.

According to various embodiments, the DNA sequencing system can comprise a plurality of nucleic acid base detection components and a memristor network. The memristor network is in electrical communication with the plurality of detectors, and can comprise a 3-dimensional network in some embodiments. In some embodiments, the memristor network can comprise a memristor/transistor hybrid network. The plurality of nucleic acid base detection components can comprise a plurality of nanopores, a plurality of nanochannels, a plurality of hybridization probes, combinations thereof, and the like. In some embodiments, the plurality nucleic acid base detection components comprises at least four detectors, and the four detectors can comprise a first detector configured to detect adenine, a second detector configured to detect cytosine, a third detector configured to detect guanine, and a fourth detector configured to detect thymine. In some embodiments, an additional detector, or one of the four detectors can be configured to detect uracil. In other embodiments, an additional detector or detectors, or one of the four detectors can be configured to detect other nucleosides such as inosine, or pseudouridine. In some embodiments, the detectors may be configured to detect any natural or synthetic nucleic acid analog. In some embodiments, the detectors can be configured to detect proteins, RNA, carbohydrates, other biomolecules, or other molecules used as markers or labels, where the protein, carbohydrate, other biomolecules, or other molecule used as a marker or label is hybridized to, bound to or associated with a portion of a single stranded or double stranded nucleic acid molecule.

According to various embodiments, the present teachings provide a method for DNA sequencing using a DNA sequencing system as described herein.

In some embodiments, memristors and/or memristor hybrid circuits perform real-time data analysis for multiple sensors at nanopore or nanochannel detection sites in a DNA sequencing system. In some embodiments, memristors and methods of using the same, that can be used according to the present teachings, include those described, for example, in Strukov et al., *The missing memristor found*, Nature, Vol 453, May 1, 2008, in Williams, *How We Found the Missing Memristor*, IEEE Spectrum, Dec. 11, 2008, in Johnson, 3-D *memristor chip debuts*, EE Times Nov. 26, 2008, and in Eid et al., *Real-Time DNA Sequencing from Single Polymerase Molecules*, published online in *Science* DOI: 10.1126/science.1162986, Nov. 20, 2008. Each of these publications is incorporated herein in its entirety by reference.

According to various embodiments, memristors, memristor/transistor hybrids, or combinations thereof, are used to collect and analyze data in real time from sensors at each of a plurality of nanochannels) or nanopore structures. In some embodiments, single, or multiple sensors in an array, are used to perform DNA sequencing. For the purposes of this disclosure "nanochannels" and "nanopores" are used interchangeably. Circuits constructed from such devices mimic aspects of the brain. Neurons are implemented with transistors, axons are implemented with nanowires in the crossbar, and synapses are implemented with memristors at the cross points. In some embodiments, such a circuit can be configured to perform real time data analysis for multiple sensors. In some embodiments, memristor crossbar memory cells are stacked on top of a CMOS logic chip. Imprint lithography can be used to add a memristor crossbar on top of a CMOS logic circuit. In some embodiments, an integrated hybrid circuit is used that comprises both transistors and memristors. Configuration bits can be located above CMOS transistors in a memristor crossbar. 3-D memristor chips comprising transistor/memristor hybrids can be used which have logic and density to perform significant real time data analysis of signals from multiple sensors, for example, multiple sensors at multiple nanopores, nanochannels, or other detectors.

An exemplary application within the scope of the present teachings is the analysis of to real-time DNA sequencing data detected at a nanopore, nanochannel, or other detection component, where the properties of the memristor or a 3-D memristor/transistor hybrid are configured to handle much more data, and more efficiently, than conventional devices. According to the present teachings, the data can be stored in memory in a non-volatile manner. In some embodiments, real-time analysis of data can be processed. The ability of memristors or memristor/transistor hybrids to act effectively in a neural network manner enables such circuits to learn and intervene in the DNA sequencing process to modify the outcome of the DNA sequencing process and make it more effective.

According to various embodiments, long-term the neural networking capabilities of memristors memristor/transistor hybrids, transistors, or tunneling electrodes enable the monitoring of fluorescent emission and non-fluorescent real-time DNA sequencing data, and can also learn. Such networks can provide feedback to the sequencing system, change DNA sequencing parameters, and render the system more efficient. For example, read lengths can be improved through improved memristor, memristor/transistor hybrids, transistors, or tunneling electrodes feedback and subsequent adjustments in the local detector environment.

According to various embodiments, real time data analysis by memristors or memristor/transistor hybrids used in a neural network fashion provides real-time feedback on the operation of one or more ZMWs or other detectors or detector components, to improve performance or alter processes and outcomes. Such systems can improve read length by opening or closing devices, adding chemicals at appropriate times, or carrying out other such operations. The memristors or memristor/transistor hybrids can be used to provide feedback real-time on data received, due to their ability to form neural networks. According to the present teachings, a network of nanopores, nanochannels, or other nucleic acid base detecting components can be integrated with memristors or memristor/transistor hybrids to form DNA sequencing systems that report in real-time and that can tune themselves the more they are used, to continuously improve base detection. The emergent behavior can result from the network processing more and more base calls and the memristor remembering the range of electrical signals detected for each of the four different bases A, C, G, and T.

In some embodiments, the system can use logic to determine whether a detected electrical signal that falls somewhere between the strength of a signal expected for a first base and the strength, duration or phase of a signal expected for a second base, so that a reliable base call can be made based on such an intermediate signal. In systems with redundancies, if the intermediate strength signal is later determined to have come from a different base than the base previously called, the system can remember how to call a subsequent base that causes a similar intermediate strength, duration or phase of a signal. Other advantages achieved from using memristors and memristor/transistor hybrids include those described in the literature incorporated herein by reference.

According to various embodiments, non-volatile storage of fluorescence emission data, ion current, tunneling current, nanoFET current, and other data obtained by multiple sensors at nanopores, or data from other detection devices can be obtained using memristors or memristor/transistor hybrids. This storage can be useful in a regulated clinical environment where the non-volatility of data can be important for legal reasons. The permanence of the memory is better in memristor devices than in most other electronic device memories.

According to various embodiments of the present teachings, hybridizable oligonucleotides referred to herein as coded molecules can be hybridized to a target DNA molecule and used to detect the presence of various sequences along the target molecule. For example, a target ssDNA molecule can be contacted with a mixture of different coded molecules and a signal resulting from an interaction with the reaction product can be detected using a nanopore, a nanochannel, a combination thereof, or the like. The hybridizable coded molecules can be selected and/or configured to effect ion current travel through a detector, for example, through an electrode pair pathway in a nanopore detector. Each coded molecule that hybridizes can cause a unique electrical signal that can be electrically, differentiated from other signals, and used to reveal information about the target. Alternatively, tunneling current, or current through a nanoFET may be used to create a differentiable signal.

Information gathered from the unique signals detected can be used to determine a portion of the sequence of the target and the position of that portion along the length of the target. The result can be a strand of DNA that is single-stranded except along respective lengths where coded molecules hybridize. Each coded molecule can hybridize to a respective stretch of the DNA strand at a respective location that is complementary to a portion of the target. By detecting different portions of the target in this manner, sequencing and/or genotyping can be performed on the target. Although the system for carrying out genotyping using such coded molecules may not necessarily be used to sequence a target in its entirety, and that a system using the coded molecules might be more accurately described as a genotyping system, it is to be understood that such a system is also referred to herein as a DNA sequencing system.

Figure 4:
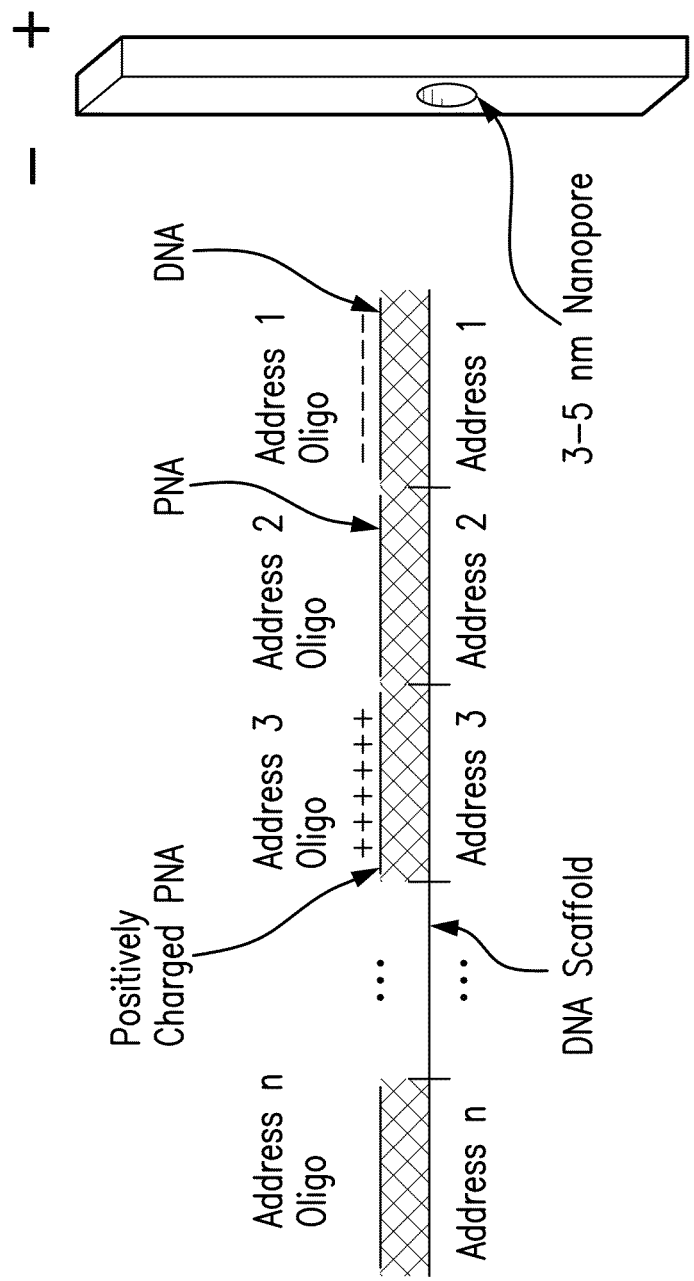
FIG. 4 is a schematic illustration of a nanopore detection system, a target molecule in the form of a single stranded DNA scaffold, and a plurality of different hybridizable coded molecules hybridized to various portions of the DNA scaffold, forming double-stranded segments along the scaffold.

An exemplary DNA sequencing system according to these embodiments will be more fully understood with reference to FIG. 4. FIG. 4 is a schematic illustration of a nanopore detection system, a target molecule in the form of a single stranded DNA scaffold, and a plurality of different hybridizable coded molecules hybridized to various portions of the DNA scaffold, forming double-stranded segments along the scaffold. As shown, coded molecules are assembled on a DNA scaffold into a linear array of oligonucleotides (oligos). The different coded molecules can be selected or made to have differential effects on ion current, tunneling current, or current through a nanoFET during traversal through the nanopore. Alternatively, in some embodiments, the detectors can be configured to detect proteins, RNA, carbohydrates, other biomolecules, or other molecules used as markers or labels, where the protein, carbohydrate, other biomolecules, or other molecule used as a marker or label is hybridized to, bound to or associated with a portion of a single stranded or double stranded nucleic acid molecule, or protein.

In FIG. 4, Address 1 refers to a specific DNA sequence. The coded molecule identified as Address 1 Oligo is an oligo having a sequence that is complementary to Address 1 so that Address 1 Oligo hybridizes to Address 1. Address 1 Oligo. A unique signal or code can be generated by configuring Address 1 Oligo to exhibit a unique ion current effect during traversal through the nanopore. As shown, Address 1 Oligo comprises a negatively charged DNA backbone, but it is to be understood that Address 1 Oligo could instead comprise a PNA backbone, a positively charged PNA backbone, or the like. If a set of different address oligos are used, they can be distinguished from one another and from stretches of non-hybridized target due to the differences in ion current detected through the nanopore. A negatively charged DNA address oligo exhibits a different current level in the measured circuit current than a neutral PNA address oligo. Likewise, a positively charged PNA would exhibit yet a third current level. Single-stranded stretches of DNA would exhibit yet another different effect on ion current and can be used to further de-code the target. Yet further current levels could be generated as a result of differences in current levels as a result of the detection of proteins, RNA, carbohydrates, other biomolecules, or other molecules used as markers or labels, where the protein, carbohydrate, other biomolecules, or other molecule used as a marker or label is hybridized to, bound to or associated with a portion of a single stranded or double stranded nucleic acid molecule, or protein. The different current levels can be analogous to different colors in a fluorescent assay. In some embodiments, current levels can result from ion currents, tunneling currents, currents in nanoFETs, or a combination of any of ion currents, tunneling currents, or currents in nanoFETs.

In some embodiments, ion current levels corresponding to single-stranded stretches of DNA are used as punctuation for the code. In some embodiments, valid codes could be followed by a distinctive current level for a single-stranded segment, for example, followed by current level indicative of a double-stranded segment. In some embodiments, valid codes could be followed by a distinctive current level for a single-stranded segment, and then followed by current level indicative of a single double-stranded segment. Detected codes that deviate from the pattern can be discarded as aberrant. In some embodiments, a first set of current levels can be used for odd addresses and a second set of current levels can be used for even addresses. Such punctuation can be used to reduce the total number of codes that can be generated for a fixed length of scaffold, and can serve as a quality control function for data analysis. In other embodiments, different types of current detection such as ion current, tunneling current or nanoFET current or any combination thereof can be utilized in a similar alternating fashion, and may thus be used to reduce the number of codes, and serve as a quality control function for data analysis In some embodiments, bulkiness is used as a property to affect ion current through a nanopore and coded molecules comprising different bulkiness can be used according to various embodiments of the present teachings. Moreover, any chemical moiety that affects, or set of chemical moieties that affect, ion current can be used in the coded molecules according to various embodiments of the present teachings. Such chemical moieties can be part of the address oligo backbone, attached to the backbone, part of the bases used to specify the sequence, or attached to the bases.

In some embodiments, the address size can be in the range of from two to 50 nucleotides (nt's), for example, from 4 to 30 nts, from 5 to 30 nts, or from 10 to 20 nts. The length of the address oligo can affect the length of time that is used to acquire an unambiguous assessment of the current level. The length of time correlating to the length of the coding molecule can also be utilized to provide unambiguous determination of the type of coding molecule, or can be utilized to increase the number of different codes available, or a combination of disambiguation and additional codes may be utilized. The length of time for an address oligo or other label to pass through the nanopore can depend, for example, on oligo length and voltage bias across the nanopore. A lower voltage bias can provide more time to get an accurate current measurement but also lowers the data collection rate. A lower voltage bias also means a lower baseline current which can affect the number of different current levels that can be distinguished. Shorter oligos and higher voltage biases are advantageous for manufacturing, high data collection rate, and larger code space, for example, more distinguishable current levels. Longer address oligos and lower voltage bias improves the quality of the current level data. The optimal selection for oligo length and voltage bias can be determined empirically and/or experimentally. In other embodiments, the speed at which the sample molecule passes through the nanopore or nanochannel can be affected by other parts of the structure.

According to various embodiments, address oligos can be used that have addresses on the scaffold right next to one another so that the finished coded molecule would be entirely double-stranded. A double stranded hybridized target could be used in an appropriately sized nanopore to traverse the nanopore in strictly a single file manner.

According to various embodiments, the coded molecules can be manufactured by encapsulating scaffold DNA molecules in vesicles or hollow beads with a semi-permeable shell. The shell can be configured to trap the scaffold DNA but permit passage of one or more address oligos. In exemplary embodiments, the scaffold molecules can be retained based on their length or due to attachment of a bulky or otherwise confining moiety. The beads can be large enough to encompass one million or more copies of the target scaffold molecule, from about 1 to about 1,000,000 copies, or from about 1 to 10,000 copies. One, tens, hundreds, thousands, or millions of beads can be used together, or more.

In an exemplary embodiment, three types of address oligos are provided: DNA−, PNA0, and PNA+. In a first step, a collection of beads is divided into three pools. The first pool of beads is incubated with the DNA+ oligos, the second pool is incubated with the PNA0 oligos and the third pool is incubated with the PNA+ oligos. After hybridization to address 1 oligo is achieved, the address oligos are cross-linked to the scaffold. Cross-linking is effected such that the oligos do not exchange during subsequent manufacturing steps or when the coded molecule is used in an assay. Next, all the beads can be mixed together and re-divided into three pools. Each of the pools can be incubated with one of the address 2 oligos followed by cross-linking. The process can be repeated until all the addresses are occupied. At the end, each bead contains a collection of coded molecules that all have the same code. To use a coded molecule collection, a bead can be broken or lysed open, a few of the molecules can be tested to determine the code, and the remainder of the molecules can be attached to the analyte-specific probes to be used in an assay. In an exemplary embodiment, for SNP detection using a ligation assay, the coded molecules can be attached to an allele-specific oligo, specific for a particular allele, for example, specific for a particular SNP.

According to various embodiments, the coded molecules can be made to pass through a nanopore or nanochannel in a strictly single file manner. The order of the coded oligos along the scaffold can be maintained and respective changes in the current single can correspond to the different oligos that pass through the nanopore. In some embodiments, modifying moieties can be attached to the target so that one particular end of the oligo can be moved first through the opening to the nanopore. Such a marker or locating moiety can be used to orient a molecule to be sequenced or genotyped. In other embodiments, a "drag chute" can be utilized such that the sample molecule is more likely to enter the nanopore or nanochannel in one direction. If order information is maintained, oligos that elicit three different current levels in a scaffold with seven addresses generate $3^7$ or 2187 different codes. For SNP analysis, two codes can be used per SNP. One code for each allele specific oligo. Thus, three current levels with seven addresses would enable analysis of about 1000 SNP's in a single multiplex reaction. For certain voltage biases, about 300-400 microseconds can be used to detect a 10 kb double-stranded DNA molecule passing through a nanopore. Accordingly, one coded molecule can be detected every 1-10 millisecond. At one millisecond, this corresponds to 1,000 molecules per second or 60,000 molecules per minute. For 2,000 different codes, 60,000 reads means that each code can be read approximately 30 times. This data redundancy is sufficient to be statistically confident whether a specific code is present or absent in a sample. Thus, the coded molecules can be read from a 1000-SNP reaction in 1-10 minutes. In some embodiments, a higher voltage bias can be utilized until a detectable change in one of an ion current, tunneling current, or nanoFET current is detected, whereupon, either the voltage bias can be changed to permit additional time for detection, or other means for changing the speed of the sample molecule through the nanopore or nanochannel can be implemented.

According to various embodiments, 1,000 genotypes in 1-10 minutes can be based on using a single detection channel. The detection apparatus can comprise a simple device comprising a chamber and two electrodes separated by a nanopore and relatively simple electronics that enable a voltage bias and a current measurement. In some embodiments, 10 or more, or 100 or more parallel channels or pores can be used such that reactions at the 1000-plex level can be analyzed on 100 parallel channels to generate detection throughput of 100,000 genotypes per 1-10 minutes. In some embodiments, the voltage bias or other means of changing the speed of the sample molecule through the nanopore or nanochannel can be implemented so that individual pores or channels can have the speed of their respective sample molecules modified.

In some embodiments, 10 different current levels are distinguished. Furthermore, lambda DNA can be used as a scaffold. In an exemplary embodiment, 20 nt addresses are used and for a 50 kb lambda DNA molecule 2500 addresses are provided. With 10 current levels, $10^{2500}$ possible codes are available. Unlimited numbers of codes are configurable.

According to various embodiments, detection across a nanopore is provided by electron tunneling, functional electrodes, atomic force microscopy, electrostatic force microscopy, combinations thereof, and the like, for example, as described herein.

According to various embodiments, a large number of coded beads can be synthesized with minimal reagents, leading to lower manufacturing costs than with individually coded bead synthesis. The length of linear coded molecules can be increased to generate unlimited code space. The detection of coded molecules is faster than the detection of coded beads, and coded molecules enable analyte assays in a homogeneous format, leading to improved kinetics. For example, according to various embodiments, ligation reactions occur more quickly in solution than they do on the surface of a bead.

According to various embodiments, the methods of the present teachings provide assays having higher sensitivity for small amounts of analytes. There is no need to maintain an optical pathway, thus increasing flexibility in instrument design and facilitating designs with multiple detection channels. Current levels can be more discrete than fluorescence emissions, leading to improved statistical power in discriminating between signals.

According to various embodiments, methods using a set of coded molecules as described herein exhibit very large code space, fast read times of discrete signals using simple instrumentation, and efficient manufacturing processes in enabling very sensitive, homogeneous analyte assays. In some embodiments, the present teachings can be implemented in connection with a digital assay format. According to various embodiments, the coded molecules of the present teachings, the methods of using them, and the kits comprising them, are useful in many applications, including, for example, detecting SNPs, quantifying mRNA, genotyping, RNA expression assays, protein expression assays, small molecule quantification assays, applications outside the field of life sciences, combinations thereof, and the like.

While exemplified with reference to nanopores, it is to be understood that the present teachings also encompass methods that use the coded molecules in nanochannel detectors and in other DNA sequence detectors.

A kit comprising mixtures of coded molecules is provided according to various embodiments of the present teachings, as are methods of sequencing and/or genotyping using the kit. The kit can comprise the coded molecules contained together or separately. The kit can also contain one or more standards, reagents, buffers, combinations thereof, and the like.

The foregoing embodiments and variations thereof within the scope of the present teachings can be implemented in or with other systems, methods, and components for DNA sequencing. Exemplary teachings with which and in which the present teachings can be implemented, and which can be implemented with and in the present teachings, include the systems, methods, and components described, for example, in Li et al., *DNA molecules and configurations in a solid-state nanopore microscope*, Nature Materials, Vol. 2, pages 611-615 (September 2003), in U.S. Pat. No. 6,464,842 to Golovchenko et al., U.S. Pat. No. 6,627,067 to Branton et al., U.S. Pat. No. 6,783,643 to Golovchenko et al., and in U.S. Patent Application Publications Nos. US 2002/0187503 A1, US 2004/0229386 A1 to Golovchenko et al., US 2008/0187915 A1 to Polonsky et al., US 2006/0084128 to Sun, US 2007/0190543 A1 to Livak, US 2007/0238186 A1 to Sun et al., US 2008/0050752 to Sun et al., US 2009/0181381 A1 to Oldham et al., and US 2009/0226927 to Sun et al., each of which is incorporated herein in its entirety by reference.

Orientation of DNA for DNA Sequencing

According to various embodiments, the DNA molecule movement device comprises a nanochannel having a first end, a second end opposite the first end, a first side or top, and an opposite side or bottom opposite the first side or top. The device comprises a pair of translation electrodes comprising a first translation electrode at the first end of the nanochannel and a second translation electrode at the second end. At least three pairs of orthogonal electrodes are arranged with each pair comprising a first orthogonal electrode at the first side or top, and a second orthogonal electrode at the opposite side or bottom.

In some embodiments, the device can be a part of a system that further comprises a control unit for individually controlling the voltage applied to at least one electrode of each electrode pair.

In some embodiments, the nanochannel is filled with an electrophoretic medium and the pair of translation electrodes can comprise a pair of electrophoretic electrodes.

According to various embodiments, an electric field control system is provided wherein peaks of an electric field in a nanochannel can be made to line-up with the periodicity of the DNA. Such fine tuning can enable desired slowing and/or stopping of the DNA. The field can be tuned to provide a net force on the DNA to slow it and/or stop it. FIGS. 5A-5C depict electrode arrangements and electric fields that can used to control the movement of the DNA. In FIGS. 5A-5C, electrode pairs 91A and 91B, 93A and 93B, and 95A and 95B are arranged along a DNA molecule manipulation channel 97 and provide electric fields collectively illustrated as 99, having a phase. A DNA molecule 101 is moved through the channel. The fields shown are not accurate but are intended to communicate the general concept of field tuning according to various embodiments.

In FIG. 5A, the phase of the electric fields and the DNA spacing are aligned and better controlled movement of the DNA target is enabled. According to various embodiments, an electric field control system can finely tune the field to adjust for variations in dimensions, environmental conditions, spacing of the DNA, and the like variables. DNA spacing can change with electrophoretic field, pH conditions, and the like, resulting in variability of phase with DNA spacing, as depicted in FIG. 5B. In some embodiments, phase alignment can be rectified by adjusting the voltage on one or more of the electrode pairs. In some embodiments, phase alignment can be rectified by directly modulating the voltage of single electrodes. After such an in-place, pre-operational adjustment or fine tuning, the phase and DNA spacing can be aligned, as shown in FIG. 5C.

In some embodiments, the migration rate of the DNA can be used as a measurement method to tune the electrode fields to the spacing needed. In some embodiments, the DNA migration is minimized with optimal field levels. The present teachings thus provide an on-the-fly tenability to a DNA molecule movement control system. The system can furthermore comprise a reversible electrophoretic field such that a DNA molecule can be made to traverse a nanochannel in a first direction, and then reverse its travel and traverse the nanochannel in an opposite direction. The repeatability enabled can provide redundancies in DNA analysis and ensure the accuracy of readings. The controlled movement can be useful, for example, in aligning a DNA molecule with a nanopore or nanochannel for further processing therein.

According to various embodiments, the present teachings provide a method for DNA manipulation using a DNA molecule manipulation system as described herein. According to various embodiments, the methods of the present teachings provide assays having higher sensitivity for small amounts of analytes. There is no need to maintain an optical pathway, thus increasing flexibility in instrument design and facilitating designs with multiple detection channels. Current levels can be more discrete than fluorescence emissions, leading to improved statistical power in discriminating between signals.

While exemplified with reference to nanochannels, it is to be understood that the present teachings also encompass methods that use nanopore detectors and other DNA base sequence detectors. According to various embodiments, detection across a nanopore can be provided by electron tunneling, functional electrodes, atomic force microscopy, electrostatic force microscopy, combinations thereof, and the like.

According to various embodiments of the present teachings, improvements are provided to the devices, systems, and methods described in U.S. Published Patent Application No. US 2008/0187915. For example, a potential barrier can be used in place of the well described, for example, by applying a negative potential to the center electrode compared to those at the sides. In such a device, the intensity of the trapping energy is not affected, and therefore neither is the viability of the device. Instead, the result is an inconsequential shift of the equilibrium position of the charges by a half inter-polymeric unit distance. In some embodiments, the barrier within a nanopore can be created by any number of electrodes, including a single electrode.

According to various embodiments, and differently from the potential well, the flexibility of a polymer can be accounted for and the electrical fields on the sides of the center electrode can be made to have a positive effect. Due to the electrical forces directed away from the center electrode, DNA passing through the fields stretches and is held under tension. Such tensional pre-loading is advantageous because the elongated DNA resembles more closely a rigid rod model and the inter-monomeric spacing useful for optimal operation of the device can be more robustly reproduced. Furthermore, the tensional pre-loading also increases the rigidity of the molecule and thus its stability, reducing detrimental effects of the Brownian motion.

In some embodiments, the elasticity of a DNA molecule can be used beneficially to compensate for manufacturing tolerances which often do not provide exact spacing with precision. Under the ideal case of a rigid rod, a dimensional mismatch would result in a reduction or zeroing of the trapping energy and, as a consequence, a reduction in the performance of the device. In some embodiments, however, by virtue of elasticity of a DNA molecule, and of the ability to control the pulling force by adjusting the potential difference between pairs of electrodes, the two sides of an ssDNA molecule can be independently stretched to match the requirements imposed by the actual size of the different layers.

According to various embodiments, a tuning process to maximize a trapping energy, for example, to find an optimal potential for each electrode, is provided based on the actual geometry of the device. In some embodiments, a feedback process can be implemented wherein voltage imposed on one or more electrodes is varied, as shown in FIGS. 6A-6C based on the resulting change of a measurable electrical property sensed by the same electrode or sensed by one or more other electrodes or sensors.

Figure 7:
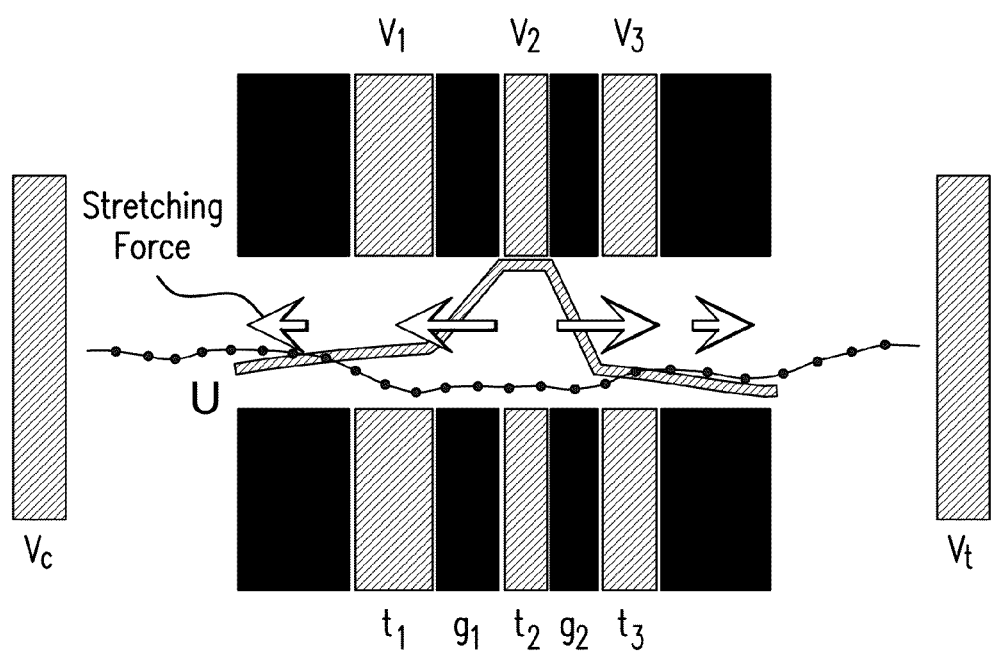
FIG. 7 depicts a DNA molecule manipulation nanopore showing three pairs of electrodes, a pair of translation electrodes, and a potential barrier, according to various embodiments of the present teachings.

In some embodiments, a potential barrier U is provided in the nanopore in place of a potential well. Such a barrier can be compatible with the superposition of an electrical field generated by the drag electrodes, as shown in FIG. 7. Although many combinations of potential profiles can be used, with the potential distribution described herein and shown in FIG. 7, the entire length of a DNA molecule within the nanopore can be placed under tension. It can be shown that the trapping action of the locking electrical fields overcomes the translocational action of the drag field. In a geometrically and electrically symmetrical case, specifically, wherein $$V1=V3 \text{ and } g1=g2$$

the result is that $$\frac{|V_1 - V_2|}{|V_t - V_c|} > \frac{g}{p},$$

where g is the gap between the electrodes and p the nominal pitch between unstretched monomeric units of the polymer.

In some embodiments, the analysis can easily be extended to the non-symmetrical case, where p1 and p2 are the effective distances along the nanopore axis between monomeric units. In various embodiments, the effective distances can be different as a result of the different pre-tensioning of the two sides of the DNA molecule. The radial positioning of the charged polymer, that is, the distance from the side walls, can be controlled by independently adjusting the biasing voltage of the potential distribution.

According to various embodiments, and similar to case with a potential well, the motion of a DNA molecule can be controlled by decreasing or eliminating the potential bather for the amount of time necessary for the DNA to move by a desired distance, before recreating the barrier. A non-zero drag electrical field allows for imparting a preferential direction for the motion of the DNA once the locking action is removed. In the case of a single potential well, the lack of controllability in the positioning of the DNA causes an inability to deterministically effect its translocation, but such problems are overcome by the present teachings.

In some embodiments, a potential barrier, a potential trap, or a combination of barriers and traps, can be cyclically shifted in time, spatially between different electrode pairs, with two electrodes being a minimum number of electrodes within the nanopore. As a result, a net motion is provided to the DNA molecule as shown in FIGS. 6A-6C. The potential barrier can be gradually changed between different electrode pairs or sets, in much the same that the magnetic field is gradually shifted in a stepper motor. Also, similar to a stepper motor, the pairs or sets of electrodes can be 180 degrees out of phase.

According to yet further embodiments of the present teachings, and similar to a stepper motor, additional pairs or sets of electrodes can be used, for example five pairs or sets, or more, can be used, similar to a five-phase stepper motor. Although five are exemplified, any other number of pairs or sets of electrodes can be used. In such embodiments, the device can be compatible with both a symmetric geometry and distribution of locking potentials, as well as with a geometrically and electrically asymmetric configuration.

In some embodiments, electrodes which are in the same position axially with respect to a motion of a DNA molecule can have the same voltage impressed upon them.

In other embodiments, electrodes which are in the same position axially with respect to the motion of the DNA molecule can have different voltages impressed upon them. As shown in FIGS. 8A-8C, the nanopore can have multiple layers and there can be one, two, three, or more electrodes and/or electrode pairs, per layer.

While exemplified with respect to nanopores, it is to be understood that such electrodes and arrangements can be configured as part of a nanochannel.

The foregoing embodiments and variations thereof can be implemented in or with other systems, methods, and components for DNA manipulation, orientation, and/or sequencing. Exemplary teachings with which and in which the present teachings can be implemented, and which can be implemented with and in the present teachings, include the devices, systems, methods, and components described, for example, in Li et al., *DNA molecules and configurations in a solid-state nanopore microscope*, Nature Materials, Vol. 2, pages 611-615 (September 2003), in the article of Ohshiro et al., *Complementary base-pair-facilitated electron tunneling for electrically pinpointing complementary nucleobases*, PNAS, Vol. 103, no. 1 (Jan. 3, 2006), in U.S. Pat. No. 6,464,842 to Golovchenko et al., U.S. Pat. No. 6,627,067 to Branton et al., U.S. Pat. No. 6,783,643 to Golovchenko et al., and in U.S. Patent Application Publications Nos. US 2002/0187503 A1, US 2004/0229386 A1 to Golovchenko et al., US 2008/0187915 A1 to Polonsky et al., US 2006/0084128 to Sun, US 2007/0190543 A1 to Livak, US 2007/0238186 A1 to Sun et al., US 2008/0050752 to Sun et al., US 2009/0181381 A1 to Oldham et al., and US 2009/0226927 to Sun et al., each of which is incorporated herein in its entirety by reference.

Velocity Control of DNA Molecule Movement for DNA Sequencing

According to various embodiments of the present teachings, a DNA molecule movement device is provided which may comprise a nanochannel having a first end, a second end opposite the first end, a top, and a bottom opposite the top. The device may further comprise at least one pair of translation electrodes, comprising a first translation electrode at the first end and a second translation electrode at the second end. A pair of orthogonal electrodes can also be provided, comprising a first orthogonal electrode at the top and a second orthogonal electrode at the bottom. A control unit can individually control the voltage applied to each of the electrodes.

In some embodiments, each of the first translation electrode and the second translation electrode each comprises an electrophoretic electrode, and the nanochannel can be filled, for example, with an electrophoretic medium. The control unit can be configured to reverse a voltage across the pair of translation electrodes, for example, to reverse a direction of movement of a DNA molecule. In some embodiments, a pair of tunneling electrodes are disposed in the nanochannel and configured to detect individual nucleic acid bases of a DNA molecule in the nanochannel.

According to various embodiments, a DNA molecule movement device is provided that may comprise: a nanochannel having a first end, a second end opposite the first end, a top, and a bottom opposite the top; a pair of translation electrodes, comprising a first translation electrode at the first end and a second translation electrode at the second end; at least one pair of orthogonal electrodes, each pair may comprise a first orthogonal electrode at the top and a second orthogonal electrode at the bottom; and a control unit for individually controlling the voltage applied to at least one electrode of each electrode pair. The control unit can comprise a feedback sensor configured to sense feedback signals related to DNA spacing and adjust the voltage, current, or both, applied to at least one of the electrodes of the at least one pairs of orthogonal electrodes. Such control can be implemented on-site after a DNA sequencing system has been set-up for operation.

According to various embodiments, a method of controlling the movement of a DNA molecule through a nanochannel is provided. The method comprises providing a DNA molecule movement device which can comprise: a nanochannel having a first end, a second end opposite the first end, a top, and a bottom opposite the top; a pair of translation electrodes comprising a first translation electrode at the first end and a second translation electrode at the second end; at least one pair of orthogonal electrodes, each pair may comprise a first orthogonal electrode at the top and a second orthogonal electrode at the bottom; and a control unit for individually controlling the voltage applied to at least one electrode of each electrode pair. The method can comprise: moving a DNA molecule through the nanochannel; detecting DNA spacing during movement of the DNA molecule through the nanochannel, to produce a signal; and adjusting the voltage applied to one or more of the electrodes based on the signal. The at least one pair of orthogonal electrodes can provide an electric field phase, and adjusting the voltage can comprise adjusting the voltage to correlate the phase with the detected DNA spacing.

In yet other embodiments of the present teachings, a method of controlling the movement of a DNA molecule through a nanochannel is provided. The method uses a DNA molecule movement device comprising: a nanochannel having a first end, a second end opposite the first end, a top, and a bottom opposite the top; a pair of translation electrodes, comprising a first translation electrode at the first end and a second translation electrode at the second end; at least one pair of orthogonal electrodes comprising a first orthogonal electrode at the top and a second orthogonal electrode at the bottom; and a control unit for individually controlling the voltage applied to at least one electrode of each electrode pair. The method may comprise moving a DNA molecule through the nanochannel in a first direction, detecting nucleic acid bases of the DNA molecule during movement of the DNA molecule through the nanochannel, and reversing the voltage applied to the first and second translation electrodes to reverse the movement of the DNA molecule to instead be in a second direction that is opposite the first direction.

According to various embodiments of the present teachings, a device is provided as is shown in FIGS. 9A-9C. The device comprises a channel 130 formed in any of a variety of ways. The fabrication approach can depend upon the method of fabrication of the electrodes to be used in the device. In the device shown in FIGS. 9A-9C, channel 130 can be etched into glass, milled into plastic, pressed into plastic, injection molded, micro-machined out of silicon, fabricated using semiconductor processes such as photolithography or nanoimprinting, or made in a like manner. Translation electrodes 132 and 134 are used to cause a DNA molecule to move from one end of channel 130 to the other end. Not shown is any opening to permit introduction of the buffer, DNA, and/or cleaning solutions into channel 130, or to remove DNA, buffer, or cleaning solutions from channel 130. The channels 130 may be fabricated in a regular or irregular 1D or 2D array (not shown), and may have common feed lines (not shown) to permit introduction of the buffer, DNA, and/or cleaning solutions into channels 130, or to remove DNA, buffer, or cleaning solutions from channels 130. Common feed lines may be co-planar with the array of channels, or may be fabricated in a parallel plane. Multiple layers of channels may also be fabricated, permitting a very high density for detection. Voltage control of electrophoretic electrodes may be common for all of an array, parts of an array, or individual electrodes may be fabricated for each nanochannel. Additional electrodes may be utilized to concentrate sample at the inlet to a nanochannel(s) relative to the common feed lines. Single electrode(s) per nanochannel(s) may be used in combination with one or more of the electrophoretic electrodes. Alternatively, a pair (or more) of electrodes may be used for each nanochannel in order to dielectrophoretically concentrate the sample at the inlet to the nanochannel(s). The dielectrophoretic electrodes may be used independently from the electrophoretic electrodes, or may be used in conjunction with one or more of the electrophoretic electrodes. It is also possible to reverse the polarity of translation electrodes 132 and 134, and or the electrophoretic electrodes, so that the DNA strand can be re-read for better accuracy. Other approaches can be utilized in place of translation electrodes to move the DNA, for example, laser tweezers (not shown). Movement can be manipulated in two axes. Arrays, either 2D or 3D, may utilized for any of the methods, systems or devices described herein, which control the movement, orientation, or detection of molecules such as DNA.

Retention electrodes 136 and 138 are utilized to immobilize or slow the DNA during reading of the bases. Tunneling current electrodes 140 and 142 are also provided. Retention electrodes 136 and 138 may cover, at a minimum, a large surface area in the area of tunneling electrodes 140 and 142. When activated, they force the DNA towards the surface where tunneling electrodes 140 and 142 are located, preventing or slowing further translation. They further reduce vibrational movement, and tend to orient the DNA, so that the base rotation between tunneling electrodes 140 and 142 is more consistent. Retention electrodes 136 and 138 can be in direct contact with the buffer solution containing the DNA, and if this is the case, tunneling electrodes 140 and 142 can be separated from retention electrodes 136 and 138 by a thin dielectric. Alternatively, it is possible to create an appropriate field by utilizing a thin dielectric between retention electrodes 136 and 138 and the buffer, and if so, the field can be increased appropriately.

Tunneling electrodes 140 and 142 can be fabricated using micromachining techniques, but could also be etched after metal deposition and e-beam lithography. They are shown as being half the height of channel 130 but can be shorter, for example, less than 100 nm, or taller, for example, the full depth of the nanochannel. Multiple sets of tunneling electrodes can be provided allowing reading at different points along the DNA strand, at once, permitting faster reading of the strand and/or better data due to averaging data between different reads. As shown, a clearance 144 is provided above tunneling current electrodes 140 and 142.

Another embodiment is shown in FIGS. 10A-10C, where reference numerals that are the same as used in FIGS. 9A-9C represent like elements. The embodiment shown in FIGS. 10A-10C is different in how tunneling electrodes 146 and 148 are generated. Rather than having one electrode on each side of the DNA, perpendicular to the backbone, tunneling electrodes 146 and 148 are created so that they cross the backbone one base apart. This embodiment is simple to fabricate and more immune to noise, as the two tunneling electrodes 146 and 148 are tightly coupled, rather than forming a comparatively large loop. Tunneling electrodes 146 and 148 do not necessarily have to be a single base apart for their entire length. Furthermore, an additional set of steering electrodes (not shown) can be provided on the walls perpendicular to tunneling electrodes 146 and 148, and can be used to center the DNA utilizing feedback from tunneling electrodes 146 and 148. In some embodiments, upper retention electrode 136 can be replaced by a pair of steering electrodes, while retaining the functionality of both. In further embodiments, steering electrodes may be utilized on the same surfaces of the nanochannel as the retention electrodes, wherein the retention electrodes do not cover the entire surface. Multiple pairs of tunneling electrodes may be utilized at once, permitting faster reading of the strand and/or better data due to averaging data between different reads.

Figure 11C:
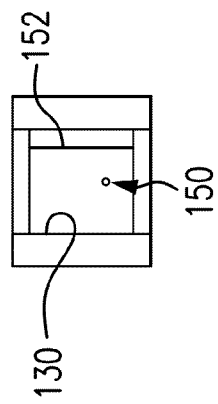
FIGS. 11A-11C are a top view, side view, and end view, respectively, of a DNA molecule manipulation channel showing electrode arrangements and a corner electrode, according to various embodiments of the present teachings.
Figure 11A:
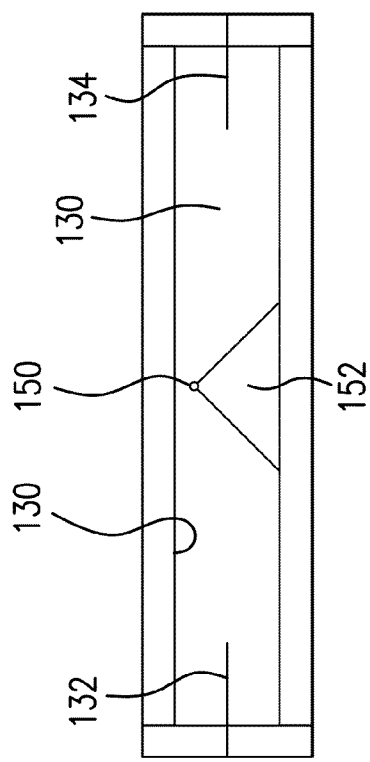
Figure 11B:
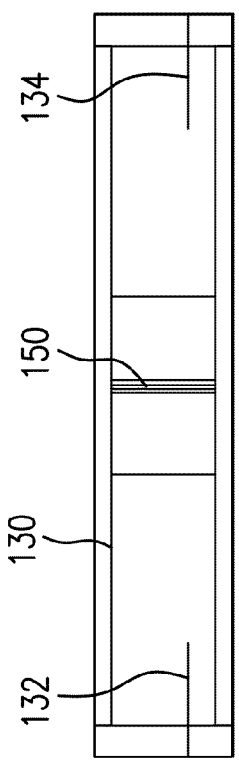

In the embodiment shown in FIGS. 11A-11C, retaining electrodes may not be used and instead a high frequency AC field is provided on the translation electrodes 132 and 134 to hold the DNA in one place. The field is also used to bring the DNA over into contact with corner tunneling electrode 150 as the DNA passes over a corner blockage 152. Corner tunneling electrode can be made to change frequency faster than the DNA can respond. This affect can be amplified by utilization of drag chutes or positively charged tails. In some embodiments, multiple corner electrodes can be created to permit multiple sets of tunneling electrodes and enable the benefits thereby accorded to detect the DNA at multiple points at once, permitting faster reading of the strand and/or better data due to averaging data between different reads. Corner electrodes may be all on one side, or may alternate sides, causing the DNA to be stretched between the different corner electrodes. In an alternative embodiment, retaining electrodes may be used in place of or in combination with the high frequency AC field to control the movement of the DNA.

FIGS. 12A-12C show an embodiment similar to that shown in FIGS. 11A-11C But comprising a channel 160 in the form of a serpentine path instead of a corner structure. Channel 160 may be of even width over its length and is shown as being sinusoidal, but can have other shapes, for example, with sharper turns. Tunneling electrodes 162 may be provided at the apex of the curves, or at other places along the curves. There may be one pair of electrodes for each curve, or there may be several pairs of electrodes for each curve.

FIGS. 13A-13C show an embodiment of a device 165 comprising a substrate 166 having a trough 168 formed therein, wherein DNA is bound in the trough. The DNA can be bound at both ends, or alternatively, at one end while the other end has a motive force applied to it such as an electric field or laser tweezers. The DNA could be bound any of a variety of means, including Biotin-Streptavidin and PNA- PNA hybridization. Stretching the DNA can be used to reduce vibrational noise. As shown the DNA is bound into the bottom of trench 168 at one end, and an electric field is applied at the far opposite end and below the end of trench 168, so that the DNA is forced into the bottom of trench 168. An AFM tip 170 is configured for use as a tunneling electrode and is scanned along trench 168. Alternatively, the DNA can be translated by moving both ends, while the AFM tip moves only in one axis. This approach can use retaining electrodes so that the DNA is held and prevented from rotating. In some embodiments, arrays of scanning AFM tips can be used in a fashion similar to that currently used for large scale memory devices.

Figure 14A:
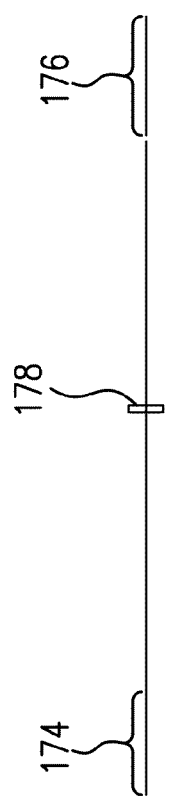
FIGS. 14A-14C are a top view, side view, and end view, respectively, of a DNA molecule stretching structure and electrode arrangement, according to various embodiments of the present teachings.
Figure 14B:
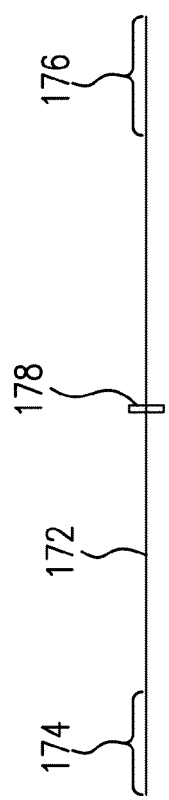
Figure 14C:
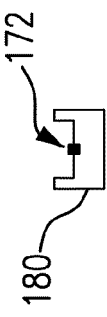

FIGS. 14A-14C show an embodiment wherein a DNA molecule 172 is actively stretched between two structures that comprise DNA binding surfaces 174 and 176. An electrode 178 is provided on both sides of the structure, one side of which is used as an AFM to determine the appropriate amount of force to apply. A second AFM is then utilized with tunneling electrodes 180 for determining the tunneling current. In some embodiments, the method can be performed in a vacuum, eliminating interference from buffer ions and water, and permitting the DNA to be deeply cooled, further reducing vibrational noise. In some embodiments, arrays of scanning AFM tips can be used in a fashion similar to that currently used for large scale memory devices.

According to various embodiments, another detection device that uses a scanning AFM approach determines the force of hybridization interaction for a short PNA, for example, a 6 mer PNA, using a large number of tips representing an appropriate set of possible 6 mers. The AFM can be oscillated perpendicular to the DNA in order to maximize the interaction. A map is then generated of hybridization force vs. position vs. sequence to determine the statistically probable sequence. Different lengths of binding moieties may be utilized, including 1, 2, 3, 4, 5, 7 or more bases.

In some embodiments, different ones of the embodiments described herein are combined, for example, by replacing the tunneling electrodes mentioned herein, with a scanning tip.

FIG. 15 is a side view of a dual-nanotube configuration according to various embodiments of the present teachings. A DNA molecule may be stretched through two carbon nanotubes 184 and 186 that function as tunneling electrodes. The distance of a single base of DNA separates nanotube 184 from nanotube 186, to define a gap 185. A tunneling current between the tubes may be used to characterize a base isolated in gap 185. Movement of DNA molecule 182 through nanotubes 184 and 186 can be effected by translation electrodes 188 and 190. In this approach, DNA molecule 182 is caused to flow through both nanotubes 184 and 186. Nanotubes 184 and 186 are then used as tunneling electrodes. The diameter of each nanotube 184 and 186 may be optimized for single stranded DNA. To optimize the reading, a rotating field can be applied to the gap between nanotubes 184 and 186 to maintain rotational consistency of DNA molecule 182. The temperature of DNA molecule 182 can be reduced, potentially significantly below 0 C in the nanotubes, while still maintaining nominally aqueous conditions. Motive forces for DNA molecule 182 include electric fields but could also or instead include processive enzymes such as polymerase or exonuclease. Additional nanotubes may be utilized, wherein a DNA molecule may traverse serially through additional nanotubes, permitting faster reading of the strand and/or better data due to averaging data between different reads. The nanotubes may be configured to be located in a nanochannel as previously described; retaining and steering electrodes may be utilized to control the movement of the DNA into nanotubes(s).

Figure 16:
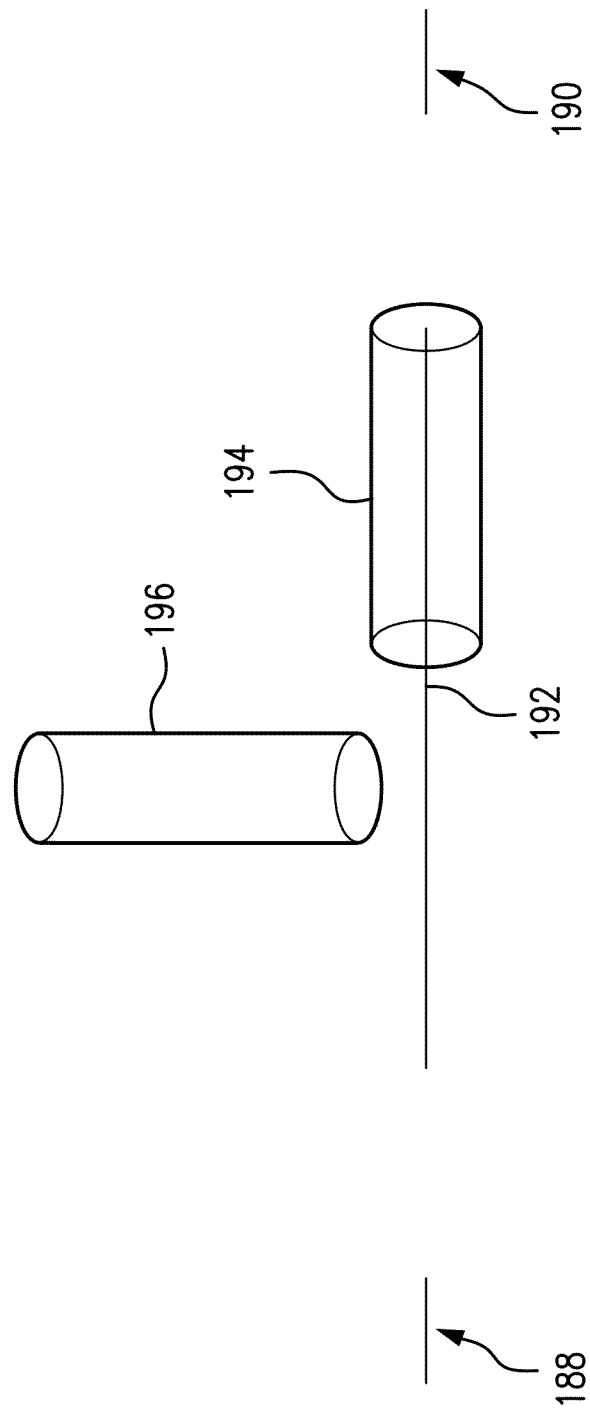
FIG. 16 is a side view of a dual-nanotube configuration according to various embodiments of the present teachings, wherein a DNA molecule is stretched through a movable nanotube tip and another carbon nanotube comprises a fixed post, a gap is configured between the fixed nanotube post and the moveable nanotube tip, the nanotube tip approaches the post from the side, and a tunneling current between the tubes is used to characterize the isolated base in the gap.

FIG. 16 is a side view of a dual-nanotube configuration according to various embodiments of the present teachings, wherein a DNA molecule 192 is stretched through a movable nanotube tip 194 and a second nanotube comprises a fixed post 196. Each nanotube can independently comprise a carbon nanotube or a nanotube made from a different material. A gap 195 is defined between fixed nanotube post 196 and moveable nanotube tip 194. As movable nanotube tip 196 approaches the fixed nanotube post 194 from the side, a tunneling current is provided between movable nanotube tip 194 and fixed nanotube post 196. The tunneling current can be used to characterize a nucleic base of the DNA molecule, isolated in gap 195. Movement of DNA molecule 192 through nanotube 194 can be effected by translation electrodes 188 and 190.

As shown in FIG. 16, the gap can be configured between fixed nanotube post 196 and moveable nanotube tip 194 that approaches fixed nanotube post 196 from the side. DNA molecule 192 can be drawn through the gap by force analogous to a rope around a pulley. A tunneling current between the fixed nanotube post 196 and the movable nanotube tip 194 can be used to characterize an isolated nucleic acid base located in the gap. DNA molecule 192 can be drawn around the fixed nanotube post 196 by optical tweezers, manipulating a bead, manipulating a magnetic bead, or the like. For a 10 nm carbon nanotube fixed post the dimension is such that only one base is exposed to the movable nanotube tip 194, at a time. In some embodiments, the fixed nanotube post diameter can be larger than the base spacing in single strand DNA. In some embodiments, the tip and post are made of material other than carbon.

Figure 17:
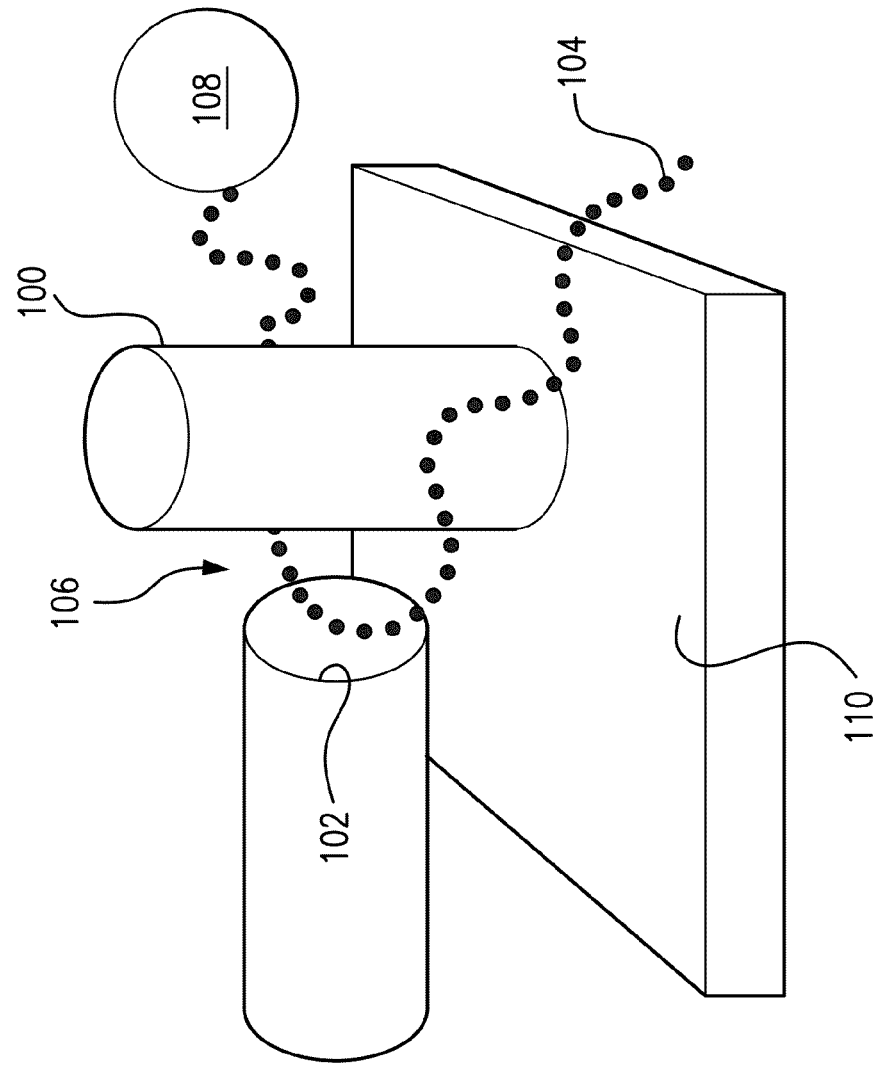
FIG. 17 is a side view of a fixed post nanotube and atomic force microscope (AFM) tip configuration according to various embodiments of the present teachings, wherein a DNA molecule is stretched around the fixed post nanotube and the gap between the fixed post nanotube and the AFM tip is configured to present just one base at-a-time to the AFM tip.

FIG. 17 is a side view of a device comprising a fixed post nanotube 100 and an atomic force microscope (AFM) tip 102 configuration according to various embodiments of the present teachings. A DNA molecule 104 is stretched around fixed post nanotube 100 and a gap 106 is defined between fixed post nanotube 100 and AFM tip 102. Gap 106 is sized and configured to present just one base at-a-time to AFM tip 102. A bead 108 can be attached to DNA molecule 104 and used to assist in manipulating movement of DNA molecule 104 through gap 106. Fixed nanotube post 100 can be part of a conductor 110. In some embodiments, the fixed nanotube may be affixed to a sharp corner or along a curve as shown in FIGS. 11A-11C and 12A-12C. In some embodiments, nanobuds may be utilized to further localize the field and tunneling current. In other embodiments, one of the nanotubes may be configured to function as a nanoFET. The nanotube may be further configured to have a nanobud in order to further localize the interaction between the DNA and the nanoFET.

Figure 18:
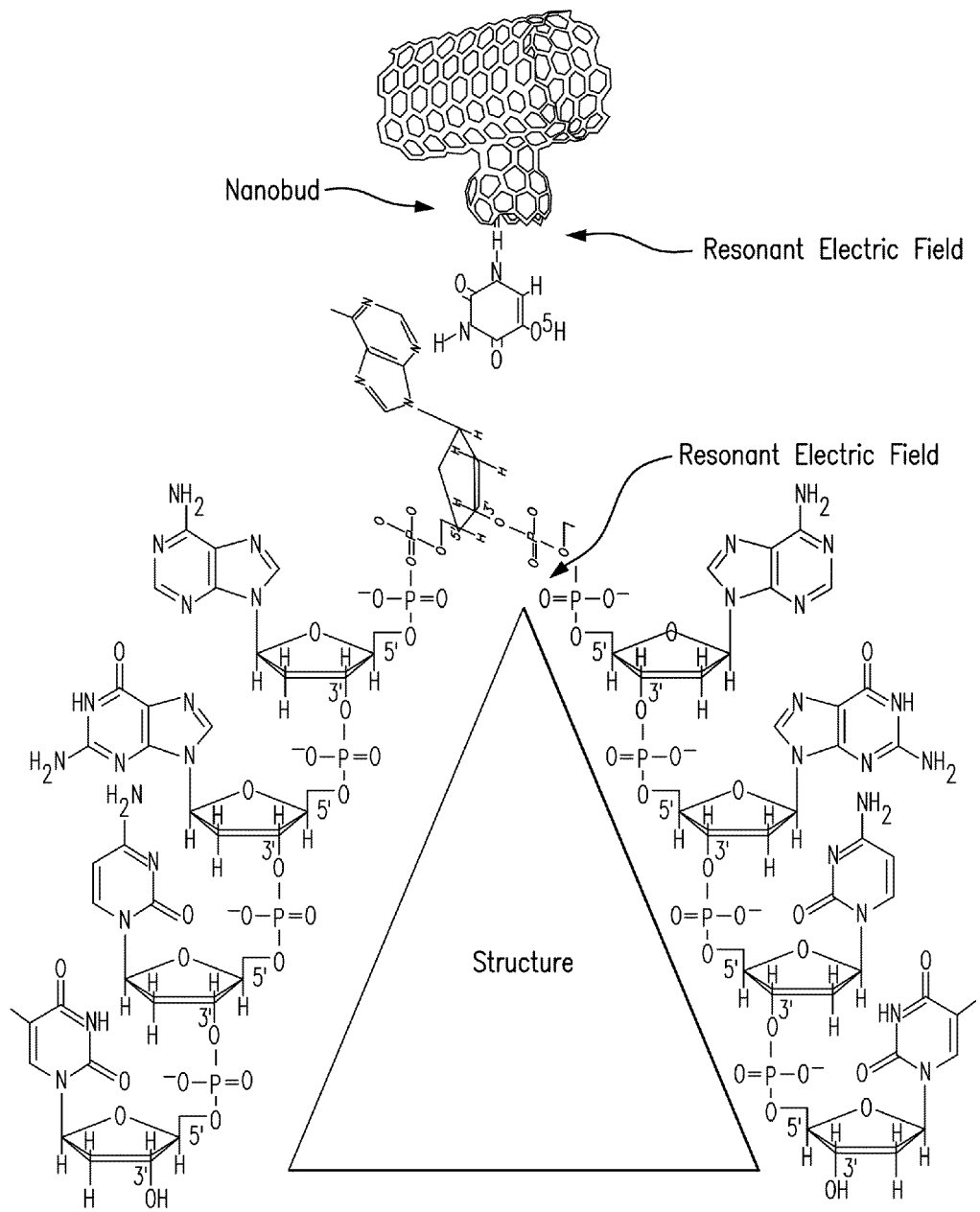
FIG. 18 is a schematic illustration of a detection scheme according to various embodiments of the present teachings wherein DNA Sequencing is carried out using a corner structure and a nanobud, and in the example shown, the nanobud is functionalized with nucleic acid receptor molecule.

FIG. 18 is a schematic illustration of a detection scheme according to various embodiments of the present teachings wherein DNA sequencing is carried out using a corner structure and a nanobud. As shown in FIG. 18, the nanobud is functionalized with nucleic acid receptor molecule. As an ssDNA molecule is manipulated around the corner structure, the individual nucleic acid bases making up the ssDNA are exposed to the nanobud. In some embodiments, four corner structures with four respective, functionalized nanobuds can be provided to sense four different nucleic acid bases.

In some embodiments, other uses of the dual nanotubes can include, among other things, observations of dye molecules, whether directly associated with DNA, or with other molecules. Nanotubes can be used to create nanoflow cells, and to cause lightwave concentration to be higher at the gap. Nanotubes with multiple carbon layers can be used in some embodiments. The gap between the dual nanotubes can function as a dipole nanoantenna to enhance single dye light emission according to a recent article by P. Muehlschlegel et al. Science 308, 1607 (2005), which is incorporated herein in its entirety by reference, and which describes using dual metal nanorods as antennae.

In some embodiments, optimizing the use of a nanopore is provided by generating a rotational field on one side of a nanopore, which may stop or slow the progress of a DNA molecule through the nanopore. In some embodiments, the field strength can be reduced so that the DNA can proceed for a single base, and then the field strength is increased again. In some embodiments, an additional rotating field is created on the opposite side of the nanopore, permitting higher field strength for better control of DNA molecule movement. In some embodiments, this concept is applied to the dual nanotube concepts described above.

According to various embodiments, an analyte detection system is provided that comprises a nanochannel having a first end, a second end opposite the first end, a top, and a bottom opposite the top. A pair of electrophoretic electrodes is provided, comprising a first electrophoretic electrode at the first end and a second electrophoretic electrode at the second end. A pair of orthogonal electrodes is also provided, comprising a first orthogonal electrode at the top and a second orthogonal electrode at the bottom. Disposed in the nanochannel are a plurality of nano-field effect transistor devices (nanoFETs) disposed in the channel. The plurality of nanoFETs can comprise at least four different nanoFETs each functionalized with a different receptor analyte than the others. In some embodiments, a target DNA molecule can be bound to a bead and the bead can be disposed in the nanochannel to hold the target molecule during a sequencing method. In some embodiments, an exonuclease enzyme can be bound to a bead and the bead can be disposed in the nanochannel.

According to various embodiments, a DNA sequencing device is provided that comprises nanoFETs which have been functionalized to detect charge changes on the surfaces of the nanoFETs. The surfaces of the respective nanoFETs can be functionalized with analyte receptor molecules exhibiting higher affinity to the intended analyte than the same nanoFETs would have without the analyte receptor molecules. In some embodiments, the receptor molecules can comprise nucleic acid base binding moieties that can temporarily bind to bases of a target nucleic acid, for example, by hydrogen binding. Such functionalized nanoFETs can be aligned in a sequential manner in a nanochannel as schematically shown, for example, in FIG. 1.

Nanopore Structures and Methods of Nucleic Acid Sequencing Using the Same

According to various embodiments, the present teachings provide functional nucleic acid base binding (affinitive) agents bound to electrodes, to detect different nucleic acid bases along a target ssDNA strand. Such detection does not need to use DNA base specific properties such as tunneling current spectrum, and the like, for detection specificity. Instead a sensing element, for example, a polymer, a nanowire, a nanotube, or the like may be used in some embodiments of the present teachings, which do not require detectors that rely on large sensitivities to changes of geometrical conformations to obtain a measurable molecular and/or structural property. Instead, functional chemical groups are attached to sensing elements, such as tunneling electrodes. The groups are specific to at least one of the different bases of the ssDNA target. In some embodiments, the sensing element is deformed by action of the moving ssDNA due to the affinity of its functional group to at least a specific base. A base-specific measurable signal can be produced from at least one electrode, or extracted from the analysis and or combination of the signals of 2 or more electrodes. In some embodiments, two or more sensing elements with different base-specificity can be integrated in the same layer of a nanopore structure. Exemplary electrodes include those described, for example, in U.S. Pat. Nos. 7,619,290, 7,595,260, 7,500,213, 7,385,267, and 7,301,199, which are incorporated herein in their entireties by reference.

In some embodiments, the nanopore can be formed in a substrate that comprises a plurality of spaced apart electrode layers each comprising a noble metal or an alloy thereof. In some embodiments, each electrode can independently comprise a metal oxide, for example, indium-tin oxide (ITO), as materials for anodes. Other metal oxide surfaces, for example, comprising $Al_2O_3$, $Ta_2O_5$, $Nb_2O_5$, $ZrO_2$, $TiO_2$, or a combination or alloy thereof, can also be used for chemically binding the affinitive agents through phosphate or phosphonate groups. The different electrode layers can be spaced apart from one another by intermediate insulating dielectric, or semiconductor layers, or combinations thereof, including combinations of different materials within the same layer, for example spaced apart by silicon nitride layers or silica layers. At least one of the electrode layers of the plurality can comprise an exposed surface that has bonded thereto a first nucleic acid base binding (affinitive) agent, and at least one different electrode layer of the plurality of layers can comprise an exposed surface that has bonded thereto a second nucleic acid base binding (affinitive) agent that is different than the first one. Each of the first and second nucleic acid base binding (affinitive) agents can comprise, for example, a thiolated polyol comprising at least one deoxyribonucleotide phosphate. The nanopore structure can be configured such that when the first or second nucleic acid base binding (affinitive) agent temporarily binds, i.e., is hybridized to, bound to, and/or associated with, a portion of the target or sample molecule. The binding can be, for example, to a complementary base of an ssDNA molecule passing through the nanopore. A change in current, voltage, or both, through the respective electrode, can be detected and used to identify the base temporarily associated.

FIG. 19 is a schematic illustration of a cross-sectional side view of an ssDNA molecule 21 being moved through a nanopore 23 according to various embodiments of the present teachings. As shown in FIG. 19, nanopore 23 comprises an inner sidewall 25 having bound thereto a trapping or entanglement polymer 26 adjacent an opening 28 of nanopore 23. The trapping polymer reduces the effective pore size of nanopore 23 and is useful to comb, stretch, and/or tension ssDNA 21 as it moves through nanopore 23. Trapping polymer 26 can be selectively immobilized to the inner sidewall of silica layer 32. Layer 32 can comprise silica or silicon with silica as in silicon dioxide derived from a natural oxidation of silicon on the exposed surface facing nanopore 23. Layer 32 can be amorphous silicon deposited by CVD. The trapping polymer can confine and tension ssDNA 21, can increase spatial sensing resolution at least by reducing buckling of the ssDNA as it moves through nanopore 23, and can decrease the effective pore size of nanopore 23. Trapping polymer 26 can comprise, for example, a dendritic polymer, a branched polymer, or a copolymer as described herein.

Nanopore 23 is formed in a substrate 30 comprising a first silica layer 32, a first silicon nitride layer 34, a first electrode layer 36, a second silicon nitride layer 38, a second electrode layer 40, a third silicon nitride layer 42, a third electrode layer 44, and a second silica layer 46. Although three electrode layers 36, 40, and 44, are depicted, more or less electrode layers can be used according to various embodiments of the present teachings. In some embodiments, the structure is free of silicon nitride layer 34. In some embodiments, there is no silicon nitride layer in between electrode layer 44 and silica layer 46. In some embodiments, the silicon nitride can be replaced by other polymer dielectrics, for example, polyimides or fluorinated poly(arylene ethers). Further details concerning the use of fluorinated poly(arylene ethers) can be more fully understood with reference to the article of Aldrich N. K. Lau et al., "Self-Crosslinkable Poly(arylene ether)s Containing Pendent Phenylenetriazene Groups," *J. Polym. Sci., Part A: Polym. Chem.*, 1994, 32, 1507-1521, which is incorporated herein in its entirety by reference.

In some embodiments, nanopore 23 is formed in a substrate 30 comprising a first electrically insulating layer 32 (e.g. silica), a second insulating layer 34 (e.g. silicon nitride), a first electrode layer 36, a third insulating layer 38 (e.g. silicon nitride), a second electrode layer 40, a fourth insulating layer 42 (e.g. silicon nitride), a third electrode layer 44, and a last insulating layer 46 (for example, silicon nitride). Although three electrode layers 36, 40, and 44, are depicted, more or less electrode layers can be used according to various embodiments of the present teachings.

As can be seen, each electrode layer has been surface-modified to have a sensing polymer 48 (e.g. electrically conductive) attached thereto. The same or different polymers can be attached to the inner sidewall surfaces of the three different electrode layers. In virtue of the confinement induced by polymers 48, 48a, and 48 of the stretching induced by polymer 26, and on the spatial arrangement of the brushes of polymers 48, 48a, and 48b, the effective separation between the electrode and the ssDNA molecule is reduced, thus originating a stronger signal and better resolution. It will be appreciated that the sensing polymers 48, 48a, and 48b provide an effective solution to relay the electrical signal between the respective electrodes and the ssDNA molecule, the former being otherwise shielded by the electric diffuse layer existing on the nanopore surface. Furthermore, polymers 48, 48a, and 48b, actively contribute to control the positioning of the ssDNA by impeding the lateral motion and dampen its Brownian motion, thus reducing the associated sensing noise. In addition, they allow for a consistent orientation of the individual bases, with the added net effect of further reducing the electrical noise associated with the random distribution and motion of the bases.

As can be seen, each electrode layer has been surface-modified to have attached thereto nucleic acid base binding (affinitive) agents 48. The same or different base binding (affinitive) agents can be attached to the inner sidewall surfaces of the three different electrode layers. As is shown at layers 36 and 44, certain bases of ssDNA molecule 21 are temporarily bound (e.g., associated) to the nucleic acid base binding (affinitive) agents attached to electrode layers 36 and 44. The temporary binding (association) can be detected by a change in current or voltage, for example, passing through the electrode. In some embodiments, different bases on the ssDNA react with different base binding (affinitive) agents to produce different changes in current which can be used to detect the type of base temporarily bound at the respective electrodes.

In some embodiments, the exposed portion of each layer can have a different chemical composition compared to the underlying material, as a result of chemical and/or physical processes occurring or performed on the surface of the pore. For example, treatments that can be used include spontaneous or non-spontaneous oxidation, such as native oxidation on silicon, chemical and/or physical post-pore formation treatments such as deposition of a thin layer of a given material, or surface activation by plasma, and the like. The exposed surface of one or more conductive layers, for example, electrode layers, can be selectively passivated or coated with a different metal, eroded, combinations thereof, and the like, by the same chemical-physical treatments mentioned above or by electro-chemical treatments. Electrochemical treatments can comprise electrodeposition, oxidation, and the like. Passivation can be used if a given electrode is to be used for capacitive sensing. A combination of passivated and non-passivated electrodes can be used if multiple sensing methods are desired. Electroplating and electro-erosion are ways to grow electrodes inside the nanopore to decrease the central gap or physical pore size and to control their shape or gap size, not only inwardly, but also outwardly. In some embodiments, an undercut electrode can be made.

FIG. 20 is a top view of nanopore 23 shown in FIG. 19, and depicts the physical pore diameter 50 and the effective pore diameter 52 resulting from the trapping polymer 26 formed on inner sidewall 25 of nanopore 23. In some embodiments, stock particles can be used to at least partially fill a nanopore to reduce the translocation rate of a molecule through the nanopore. In some embodiments, melted and drawn polymers can be formed and used to reduce the effective pore size of the nanopore. Melted and drawn polymers can be coated on top of a substrate through which a nanopore is formed, and can partially block the nanopore, for example, at its opening. Polystyrene, polypropylene, polyethylene, and the like, polymers can be used for such purpose according to various embodiments. FIG. 20 depicts the physical pore diameter 50 at the level of electrode 44, and the effective pore diameter 52 that can result from a sensing polymer 48b formed on inner sidewall 25 of nanopore 23.

FIG. 21 is a schematic illustration of a cross-sectional side view of an ssDNA molecule 58 being moved through a nanopore 60 according to various embodiments of the present teachings. Nanopore 60 comprises a first nucleic acid base binding (affinitive) agent 62 bound to an inner sidewall surface of an electrode 63, and a second, different, nucleic acid base binding (affinitive) agent 64 bound to an inner sidewall of a different electrode 65. In some embodiments, the exemplary multilayered structure 66 can be repeated to provide many layers of electrodes surface modified with different nucleic acid base binding (affinitive) agents. At least one electrode layer can be provided to detect each of the four different nucleic acid bases A, C, G, and T. The number of electrode layers can be dictated by the sequencing redundancy required and the base-resolvability of each individual electrode, for example, the minimum number of electrodes required to resolve the four bases.

FIG. 22 is a top view of nanopore 60 shown in FIG. 21, and shows an electrode 68 and a counter-electrode 69 spaced apart by dielectric spacers 70 and 71. As can be seen, the electrode 68 can have a much larger exposed inner sidewall than counter-electrode 69, for example, from 50% larger to 400% larger, from 100% larger to 300% larger, or from 200% larger to 250% larger. In various embodiments, the counter-electrode can lay on a different layer, or as a counterelectrode one of the electrodes of a different layer can be used, or even an electrode not embedded in the nanopore. Also, the function of the electrode and counterelectrode can also be inverted. As shown in this drawing, a counterelectrode can be naked (i.e. without immobilized polymers), but it can also have a polymer immobilized on its surface as well. In summary, a layer can contain one or more electrodes, and one or more counterelectrodes, with or without immobilized polymers, and their function can be inverted as well as their pairing can be rearranged during the operation. Equally, pairing between electrodes and counterelectrodes on different layers, with or without immobilized polymers, is also possible, as well as their functional inversion or pairing rearrangement at run time.

FIG. 23 is a schematic illustration of a cross-sectional side view of an ssDNA molecule 78 being moved through a nanopore 80 according to yet other various embodiments of the present teachings. Nanopore 80 comprises four different selective nucleic acid base binding (affinitive) agents 82, 84, 86, 88, configured to bind with the four different nucleic acid bases A, C, G, T. Base binding (affinitive) agents 82, 84, 86, and 88 are bound to four different respective electrodes 92, 94, 96, and 98. FIG. 24 is a top view of the nanopore and molecule shown in FIG. 23, taken along line 6-6 of FIG. 23, and showing the arrangement of electrodes 92 and 94. A single counter-electrode 101 is provided. Electrodes 92 and 94, and counter-electrode 101, are spaced apart from one another by dielectric spacers 103, 105, and 107. The dielectric spacers can be made of polymer dielectric materials, for example, polyimides or fluorinated poly(arylene ethers).

Figure 25:
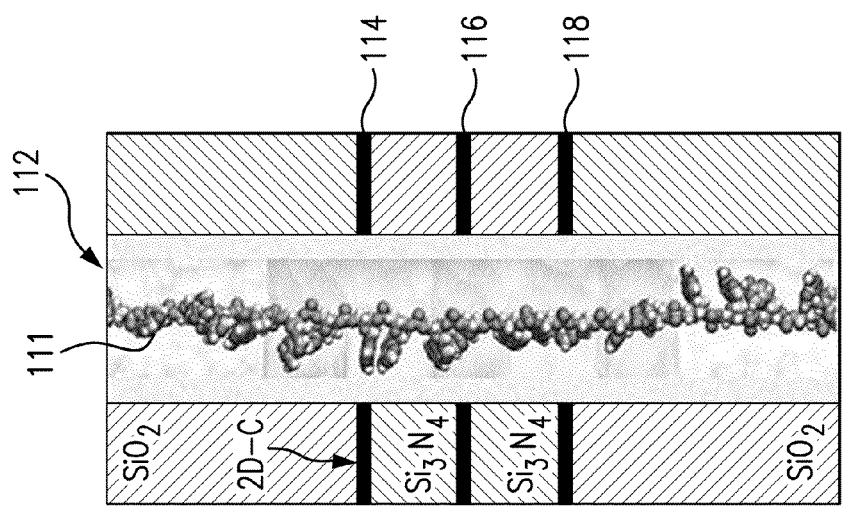
FIG. 25 is a schematic illustration of a cross-sectional side view of an ssDNA molecule being moved through a nanopore according to various embodiments of the present teachings, wherein the nanopore comprises individual single layers of grapheme.

FIG. 25 is a schematic illustration of a cross-sectional side view of an ssDNA 111 molecule being moved through a nanopore 112 according to various embodiments of the present teachings. Nanopore 112 comprises selective nucleic acid base binding (affinitive) agents (not shown) bound to surfaces of two-dimensional carbon electrode layers 114, 116, and 118. As shown, electrode layers 114, 116, and 118 are spaced apart from one another by dielectric layers comprising silicon nitride or a dielectrics polymer. Electrodes 114, 116, and 118 are graphene, which, by virtue of its single layer thickness and its electrical properties, provides superior resolution and electrical transduction. Nanopore 112 can also comprise selective nucleic acid base sensing agents (not shown) bound to the exposed atoms of the graphene layers 114, 116, and 118.

According to various embodiments, a nanopore can be provided with a geometry therein that makes the nanopore asymmetrical. An asymmetry can be provided in the nanopore that causes a molecule, for example, a ssDNA molecule, to twist as it translocates through the nanopore. The amount of torque applied to the molecule, to move through the pore, can be measured. As each base of an ssDNA molecule negotiates past the asymmetry, a distinct torque can be applied and measured, and the molecule can thus be sequenced. In some embodiments, magnetic beads can be tethered to two opposite ends of a molecule, the two ends can be stretched apart, and the rotation and/or torque resulting from moving each nucleic acid over or past the asymmetry can be measured, and the base characteristic of that torque can be determined.

According to various embodiments, a method is provided that comprises providing and/or forming a nanopore through a substrate that comprises at least one layer of graphene. The nanopore can comprise an inner sidewall, at least a portion of which comprises an exposed graphene surface. The exposed graphene surface can be modified by a reaction that covalently binds thereto a nucleic acid base binding (affinitive) agent. The binding (affinitive) agent can comprise a carbonyl linkage moiety and a deoxyribonucleotide phosphate. In some embodiments, the phosphate can comprise a diphosphate or a triphosphate.

Figure 26:
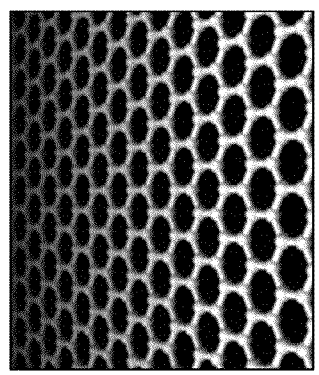
FIG. 26 is a schematic illustration of a graphene layer that can be used as an electrode layer according to various embodiments of the present teachings.
Figure 27:
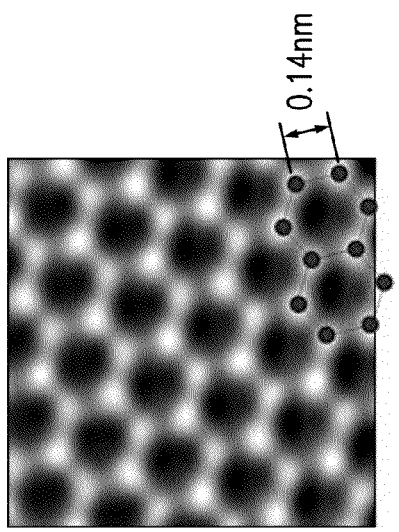
FIG. 27 is an enlarged view of a portion of FIG. 26, showing the average distance between nuclei in the graphene layer.

FIG. 26 is a schematic illustration of a graphene layer that can be used as a two-dimensional carbon electrode layer according to various embodiments of the present teachings. FIG. 27 is an enlarged view of a portion of FIG. 26, showing the average distance between nuclei of adjacent carbon atoms in the graphene layer. Using graphene can provide atomically thin electrodes. Minimizing electrode thickness can improve resolution and can be used with many of the functionalized nucleic acid base binding (affinitive) agents described herein. Graphene can be used for on-chip integration of both molecular sensing and signal processing electronics. Further details concerning the use of graphene can be more fully understood with reference to the article of Yu-Ming et al., *Operation of Graphene Transistors at Gigahertz Frequencies*, published by IBM T.J. Watson Research Center, Yorktown Heights, N.Y. (Dec. 19, 2008), which is incorporated herein in its entirety by reference.

Figure 28:
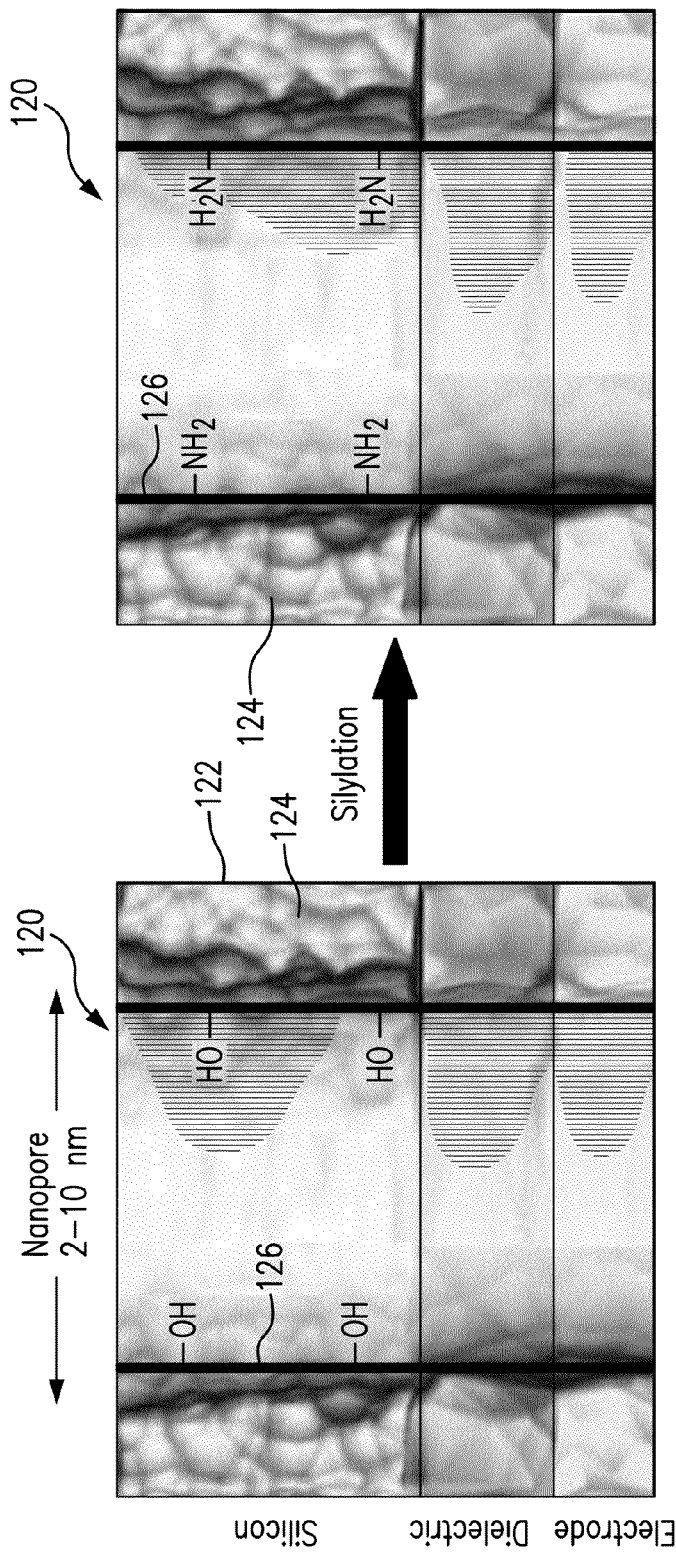
FIG. 28 is a cross-sectional side view of a nanopore surface modification method that can be used in preparing a nanopore according to various embodiments of the present teachings, wherein silanol groups on the exposed inner sidewall of a silica layer are subject to amino silylation.

According to various embodiments, a method of forming a nanopore structure is provided. FIG. 28 is a cross-sectional side view of a nanopore surface modification method that can be used in preparing a nanopore according to various embodiments of the present teachings. The method can comprise treating a nanopore 120 that is formed through a substrate 122 comprising at least one layer of silica material 124. Nanopore 120 can comprise an inner sidewall 126 having exposed silanol groups. The exposed silanol groups can be reacted with an amino-containing alkoxysilane to convert the silanol groups to amino groups. FIG. 28 depicts such a reaction. As shown silanol groups on the exposed inner sidewall of a silica layer are subject to aminosilylation.

Figure 29:
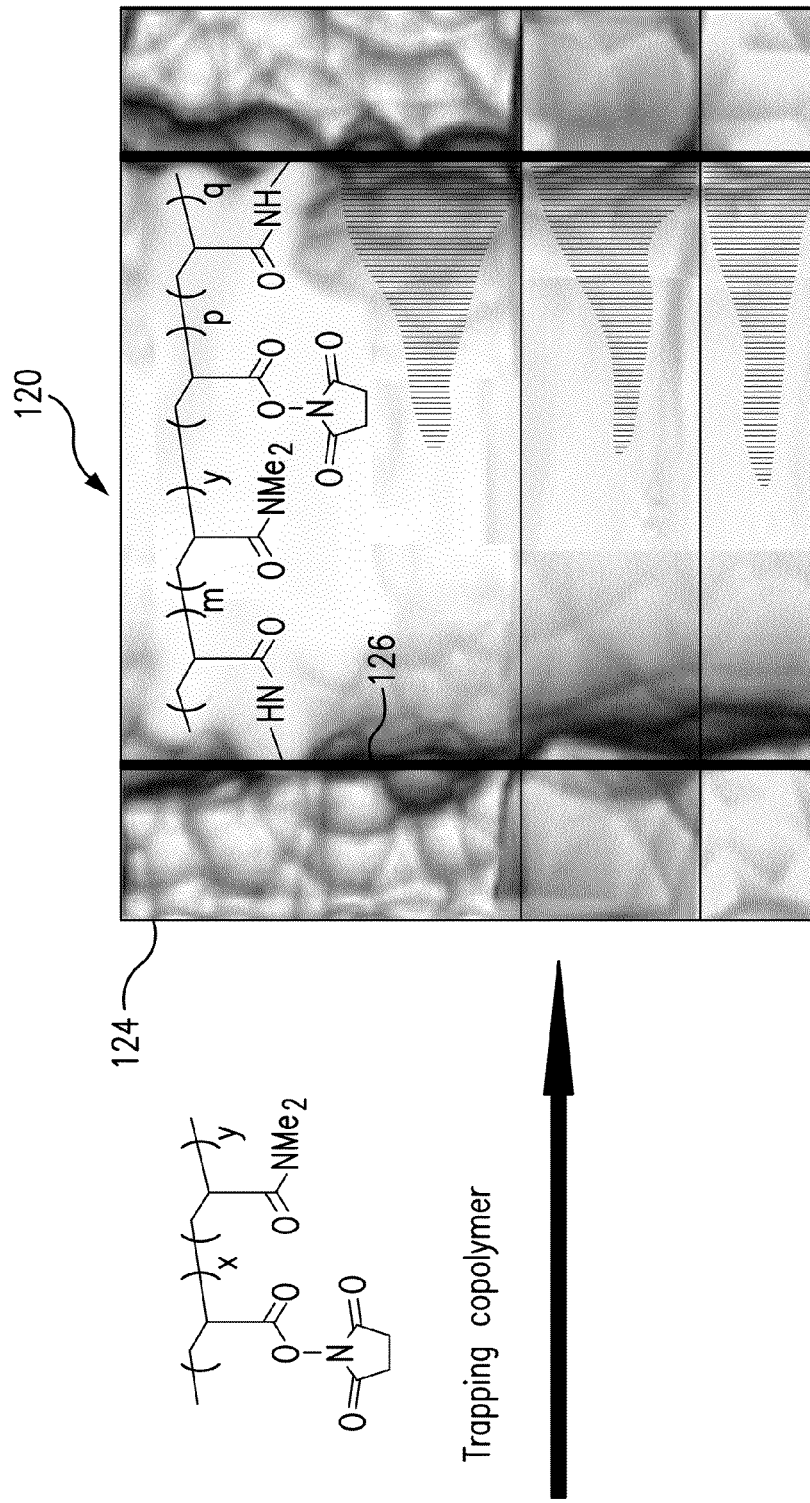
FIG. 29 is a cross-sectional side view of a nanopore surface modification method that can be used in preparing a nanopore according to various embodiments of the present teachings, wherein a trapping or entanglement copolymer is chemically bonded to the exposed inner surface of the nanopore shown in FIG. 28 by reacting the reaction product of an N-hydroxy succinimide ester of acrylic acid and N,N-dimethylacrylamide with the amino groups on the exposed surface.

The amino groups thus formed can be reacted with the copolymerization product of an acrylic acid ester of N-hydroxysuccinimide and N,N-dimethylacrylamide. FIG. 29 is a cross-sectional side view of a nanopore surface modification method wherein a trapping or entanglement copolymer is bonded to the exposed inner surface of nanopore 120 by reacting the reaction product of an acrylic acid ester of N-hydroxysuccinimde and N,N-dimethyl acrylamide with the amino groups on exposed inner sidewall 126, formed by the method step depicted in FIG. 28. The reaction results in the copolymer covalently bonded on exposed inner sidewall 126.

Different molecular weights can be used to fine tune the amount of trapping or entanglement that can be provided. Molecular weights in the range of from 0.1 to 10 MDa, 0.75 to 5 MDa, or 1 MDa to 2 MDa can be used. For example, a trapping copolymer having a weight of about 1.0 MDa can be used to reduce the effective pore size of a 10 nm nanopore. In some embodiments, the trapping copolymer can be spin-cast into the nanopore.

In some embodiments, the copolymerized product can be cross-linked by reacting its residual acrylic acid ester of N-hydroxysuccimide with an $\alpha,\omega$-diamino polyol (PEG) to form a cross-linked product that further increase Trapping/entanglement to slow or tension the translocation of ssDNA in the nanopore.

Figure 30:
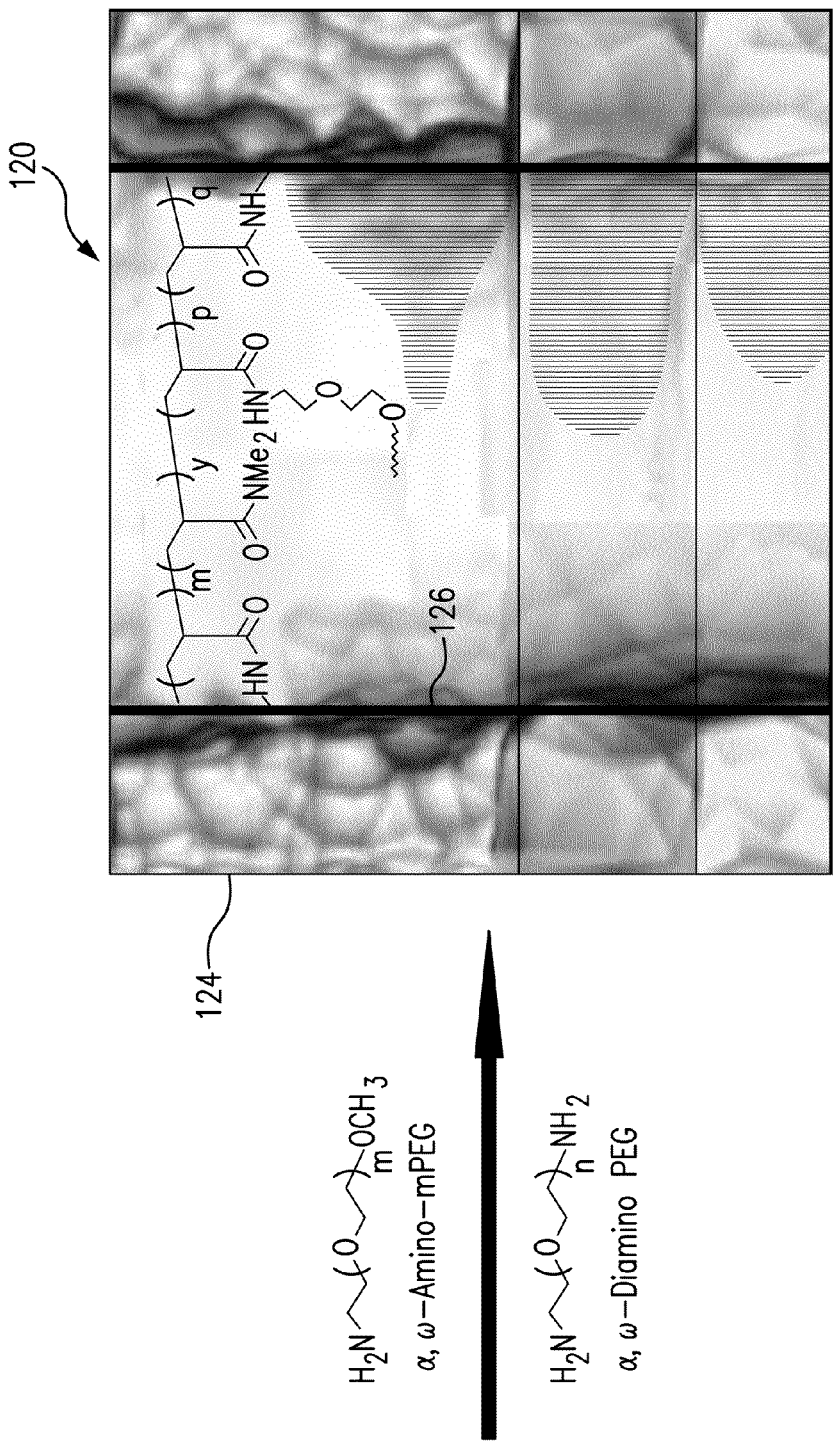
FIG. 30 is a cross-sectional side view of a nanopore surface modification method that can be used in preparing a nanopore according to various embodiments of the present teachings, wherein the trapping or entanglement copolymer on the inner sidewall of the nanopore shown in FIG. 29 is further capped with an amino-terminated polyol and/or crosslinked with a diamino terminated polyol.

FIG. 30 is a cross-sectional side view of nanopore 120 after a subsequent surface modification wherein the residual acrylic acid ester of N-hydroxysuccinimde in the trapping or entanglement copolymer (as shown in FIG. 29) on exposed inner sidewall 126 is further modified. As shown in FIG. 30, the further an amino-terminated polyethylene glycol can be used to react with the unreacted acrylic acid ester of N-hydroxysuccimide to further increase polymer entanglement. An $\alpha,\omega$-diamino polyol (PEG), can also be used, in conjunction or alone, to react with the unreacted acrylic acid ester of N-hydroxysuccimide resulting in a crosslinked 3-D network to improve trapping characteristics.

The resulting surface treatment polymer can be useful for slowing down translocation of an ssDNA molecule through the nanopore, and for stretching out the ssDNA as it passes through the nanopore. Individual bases of the stretched out ssDNA can thus be more readily detected by detection moieties in the nanopore, compared to when detection of the bases in a non-stretched conformation.

The esterified acrylic acid can comprise an N-hydroxy succinimide ester of acrylic acid, an N-hydroxy succinimide ester of methacrylic acid, or the like. The acrylamide can comprise methyl acrylamide, N,N-dimethyl acrylamide, or the like.

In some embodiments, a water-soluble capping agent and cross-linker can be used. In some embodiments, a functional capping agent can be used to provide not only trapping but also selective nucleic acid base sensitivity. In some embodiments, N-isopropylacrylamide can be used in place of, or in addition to, N,N-dimethylacrylamide, to provide LCST characteristics.

According to various embodiments, a method is provided for surface modification of a nanopore through a substrate that comprises at least one layer of a noble metal or a noble metal alloy, used as an electrode layer. The electrode layer can, for example, be electrically connected to a voltage source and an applied potential can be used that renders the electrode an anode. At least a portion of an inner sidewall of the nanopore can be defined by an exposed surface of the at least one layer. In some embodiments, the electrode can comprise gold. According to various embodiments, the exposed noble metal or alloy thereof can be reacted, at the exposed surface thereof, with a thiolated compound, such that a sulfur linkage to the exposed surface is formed. The thiolated compound can comprise a deoxyribonucleotide triphosphate moiety, or the like. In some embodiments, the method can further comprise reacting the thiolated compound with a deoxyribonucleotide triphosphate prior to reacting the thiolated compound with the exposed surface, and in other embodiments, such a reaction can be caused after reacting the thiolated compound with the exposed surface.

In use, a potential can be applied to the exposed surface to create an anode. In an exemplary embodiment, the noble metal or noble metal alloy comprises gold, for example, pure gold or gold having a purity of greater than 95% by weight. For reactions to an exposed gold surface, the thiolated compound can comprise a thiolated polyethylene glycol. For example, the thiolated compound can comprise an amino group linked to a mercapto group by a poly(ethylene oxide) linker. In some embodiments, the method begins by forming the nanopore before it is treated. Forming can be by chemical etching, plasma etching, ion etching, laser drilling, micromachining, or the like.

Figure 31:
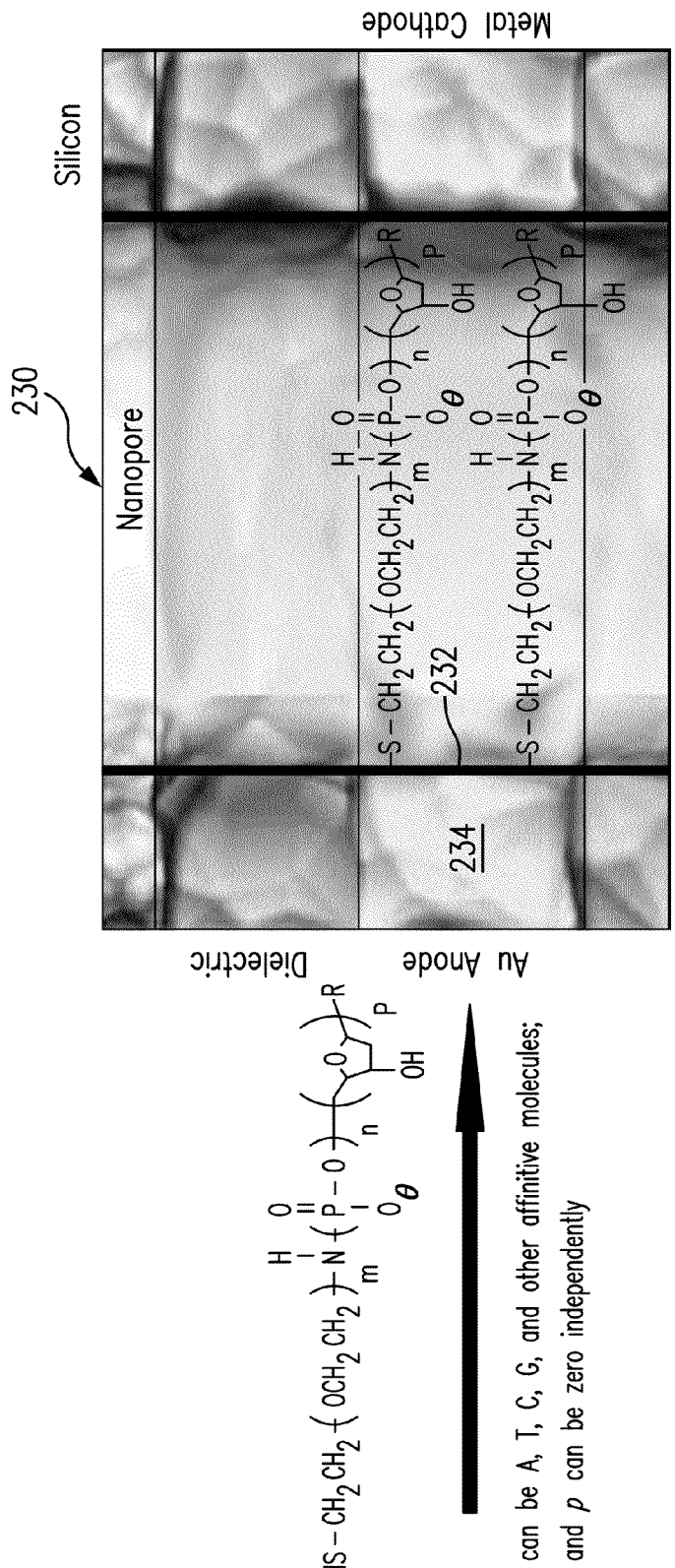
FIG. 31 is a cross-sectional side view of a nanopore surface modification method that can be used in preparing a nanopore according to various embodiments of the present teachings, wherein an exposed inner sidewall of a gold anode layer of a nanopore is subject to surface modification by reaction with a thiolated nucleic acid base binding (affinitive) agent.
Figure 33A:
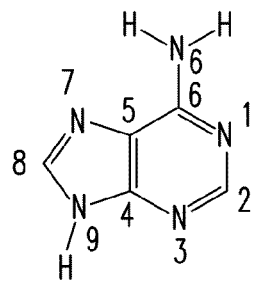
FIGS. 33A-33D show the chemical structures of four respective nucleic acid binding (affinitive) agents that can be reacted with various sugar/phosphate moieties and thiolated polyols as described herein to conjugate nucleic acid binding (affinitive) agents being bound by a thiol linkage to the surface of a gold anode, according to various embodiments of the present teachings.
Figure 33B:
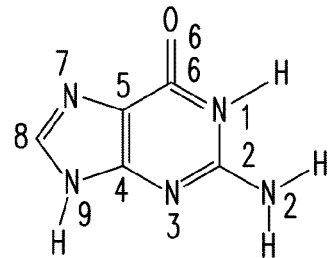
Figure 33C:
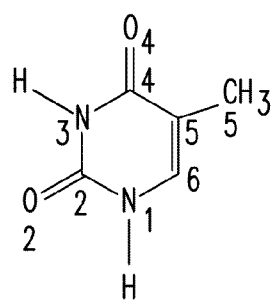
Figure 33D:
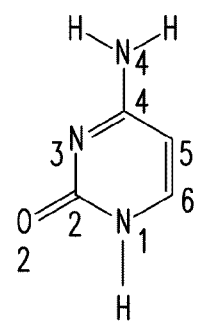

FIG. 31 is a cross-sectional side view of a nanopore surface modification method that can be used in preparing a nanopore according to various embodiments of the present teachings. An exposed inner sidewall 232 of a gold anode layer 234 of a nanopore 230 is subjected to surface modification by reaction with a thiolated nucleic acid base binding agent. One or more different nucleic acid binding (affinitive) agents can be bound to exposed inner sidewall 232 of gold anode 234. In the chemical formula shown in FIG. 31, m, n and p can each independently be 0, from 1 to 100, from 1 to 50, from 1 to 20, from 1 to 10, or from 1 to 5. FIGS. 32A-32F show the chemical structures of six respective thiolated polyols that can be used in the formation of a nucleic acid binding agent on inner sidewall surface 232 of gold anode 234 shown in FIG. 31, according to various embodiments.

Figure 34:
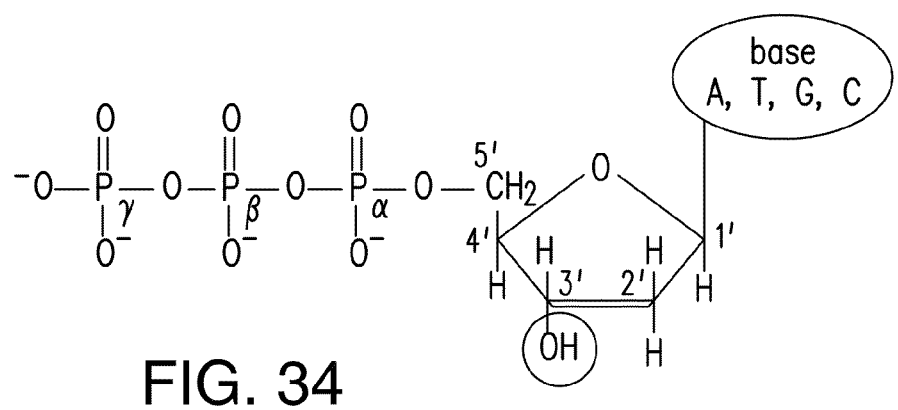
FIG. 34 shows a deoxyribonucleotide triphosphate that can include one of the bases shown in FIGS. 33A-33D and may be used as a nucleic acid binding (affinitive) agent according to various embodiments of the present teachings.

FIGS. 33A-33D show the chemical structures of four respective nucleic acid binding (affinitive) agents that can be reacted with various sugar/phosphate moieties and thiolated polyols as described herein to form nucleic acid binding (affinitive) agents being bound by a thiol linkage to inner sidewall surface 232 of gold anode 234 shown in FIG. 31. One such sugar phosphate moiety having a base as shown in FIGS. 33A-33D is shown in FIG. 34. In some embodiments, each base binding (affinitive) agents can comprise one of the moieties shown in FIGS. 33A-33D bound to the remainder of the binding agent through the 9-N atom (as with Ade and Gua) or through the 1-N atom (as with Thy and Cyt). In some embodiments, functional groups can be bound to the remainder of the base binding agent with sugar groups, with phosphate groups, or through polyA, polyC, polyG, and polyT (U) moieties. In other embodiments, one of the moieties shown in FIGS. 33A-33D bound to the remainder of the binding agent through the 9-N atom (as with Ade and Gua) or through the 1-N atom (as with Thy and Cyt) can be bound directly to a carbon graphene layer, without a linker.

FIG. 34 shows a deoxyribonucleotide triphosphate that can include one of the bases shown in FIGS. 33A-33D in the position indicated, to form a nucleic acid binding agent according to various embodiments. The binding agent can temporarily bind with a complementary base of a target ssDNA strand as the target strand is moved through nanopore 230 shown in FIG. 31. The temporary binding can comprise, for example, the formation of hydrogen bonds, van der Waals forces, a combination thereof, or the like, resulting in a change in current that can be detected and used to identify the base that temporarily bound to the base binding (affinitive) agent.

Figure 35:
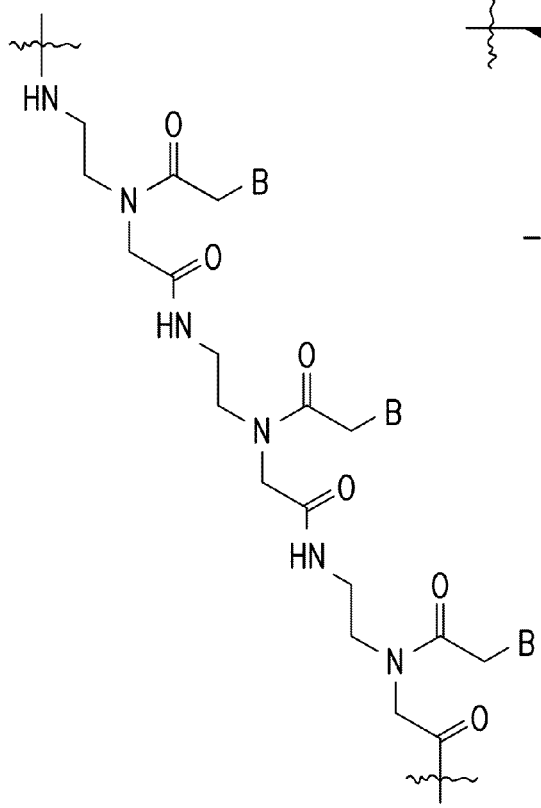
FIGS. 35 and 36 show a PNA moiety and a DNA moiety, respectively, that can be used in forming a nucleic acid binding (affinitive) agent according to various embodiments of the present teachings.
Figure 36:
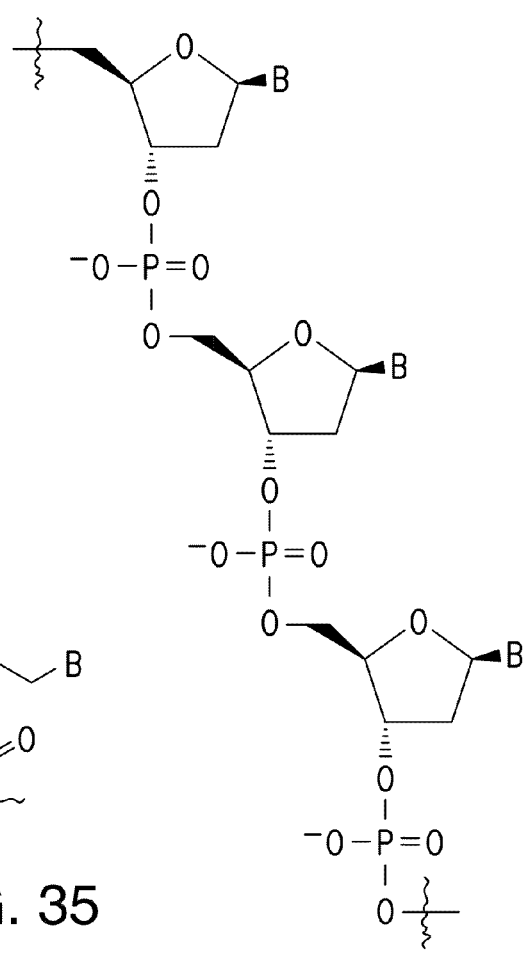

FIGS. 35 and 36 show a PNA moiety and a DNA moiety, respectively, that can be used in forming nucleic acid base binding (affinitive) agents according to other various embodiments of the present teachings.

The nucleic acid base binding (affinitive) agents can be put on respective electrodes in a controllable manner, using electrochemical immobilization. In some embodiments, the binding (affinitive) agents can be moved by charge attraction/repulsion and covalently bonded into place.

According to yet other embodiments of the present teachings, a nanopore formed through a substrate is provided. The nanopore can comprise an inner sidewall and can have a diameter. The inner sidewall can be surface-modified to have bound to the surface thereof a polymer extending radially inwardly, for example, toward the radial center of the nanopore. The polymer can extend inwardly by a distance that is at least 25% of the length of the diameter, for example, about 35, about 45%, or about 55% of the length of the diameter. The inner sidewall can be surface-modified to have bound to one side of the surface thereof a polymer extending itself across the length of the diameter to the opposite side of the pore. The inner sidewall can also be surface-modified to have multiple points of bonding to the surface thereof a polymer extending to cover the pore opening at various levels. The diameter can be 100 nm or less, for example, 20 nm or less, or 10 nm or less. The polymer can comprise any of the nanopore surface-modifying polymers described herein, for example, the polymer can comprise a reaction product of an esterified acrylic acid and an acrylamide, a reaction product of a thiolated compound comprising a deoxyribonucleotide phosphate moiety, a reaction product of a carboxylic acid comprising a deoxyribonucleotide phosphate moiety, or the like.

In yet other embodiments of the present teachings, a multilayer nanopore is provided, that is formed in a substrate. The nanopore can comprise an inner sidewall defined, at least in part, by a first layer. The first layer can comprise an exposed surface at the inner sidewall. In some embodiments, the exposed surface can define an electrode, one or more counter-electrodes, and one or more dielectrics that separate the electrode from the one or more counter-electrodes. In some embodiments, at least two counter-electrodes are defined at the nanopore inner sidewall and each can be surface-modified with a different nucleic acid base binding (Affinitive) agent covalently bonded thereto at the exposed surface. With such a configuration, either of at least two different nucleic acid bases can be identified by the first layer electrodes. Configurations having multiple different layers of electrodes can be used to detect all possible nucleic acid bases and/or to provide detection redundancies useful to verify results.

In use, an electrokinetic force such as an electrophoretic field can be applied through the nanopore, for example, using an electrode pair comprising an electrode above the nanopore and a counter-electrode below the nanopore. The field can be arranged, and of such strength, that ssDNA molecules will translocate through the nanopore from one side to the other. A reversible field can be configured such that the ssDNA can be drawn through the nanopore in a first direction, and then through the nanopore in an opposite direction. Such a configuration enables sequencing detection in either and both directions. A back-and-forth approach can be used to provide redundancies in the base calling signals, for example, double checking or base calling in forward and reverse directions. Signal processing can be used to throw out bad signals, deconvolute signals, accumulate signals, make base calls, perform combinations of such processes, and the like.

According to various embodiments, non-aqueous solvents can be used as a media through which target nucleic acids can be moved. Advantageously, when using non-aqueous solvents, no hydrolysis occurs and there is a broader operating voltage window. Non-aqueous solvents can also provide lower background noise, a cleaner electrical signal, and a better signal to noise ratio (S/N). The non-aqueous solvent does not necessarily have to be a good DNA solvent as electrophoretic stretching can make up for natural relaxation of the target molecule. Moreover, non-aqueous solvents can be used that have optimal viscosity for DNA translocation. The non-aqueous solvent can be, for example, acetonitrile, DMF, DMSO, or lactam.

Methods of improving oriented movement of a nucleic acid strand through the nanopore can be facilitated by adding relatively large molecules, or a macromolecule, to the nucleic acid being sequenced. Such macromolecules can, for example, be attached to one end of an ssDNA fragment, resulting in a hydrodynamic drag force in a direction that is opposite the direction of the electric driving force. The macromolecule can comprise a polymer and can be neutral or charged and its molecular weight does not need to be monodispersed, i.e., Mw/Mn does not have to be equal to 1. Exemplary macromolecules that can be used for this purpose include those described, for example, in U.S. Patent Application Publications Nos. US 2008/0241950 A1 to Meagher et al. and US 2008/0227211 A1 to Meagher et al., both of which are incorporated herein in their entireties by reference.

Other references that have devices, systems, methods, and chemistries that can be implemented in conjunction with and as part of the present teachings include U.S. Published Patent Application No. US 2008/0187915 A1 to Polonsky et al., publication WO 2008/092760 A1 to Polonsky et al., the article of Morpurgo et al., *Controlled fabrication of metal electrodes with atomic separation, American Institute of Physics*, Volume 74, No. 14, pages 2084-2086 (1999), and the IBM Research Report of Polonsky et al., *DNA Transistor*, IBM Research Division, RC24242, W0704-094 (Apr. 18, 2007), which are incorporated herein in their entireties by reference.

Other embodiments of the present teachings will be apparent to those skilled in the art from consideration of the present specification and practice of the present teachings disclosed herein. It is intended that the present specification and examples be considered exemplary only.

What is claimed:

1. An analyte detection system comprising:
   a fluidic nanochannel having a first end, a second end opposite the first end, a first side, and a second side opposite the first side;
   a pair of electrophoretic electrodes, comprising a first electrophoretic electrode at the first end and a second electrophoretic electrode at the second end;
   a pair of orthogonal electrodes, comprising a first orthogonal electrode at the first side and a second orthogonal electrode at the second side; and
   a plurality of nano-field effect transistor devices (nanoFETs) disposed in the fluidic nanochannel, wherein the plurality of nanoFETs comprise at least four different nanoFETs each having a gate electrode functionalized with a receptor including a nucleoside or a protein nucleic acid, the at least four different nanoFETs including a nanoFET to detect adenine, a nanoFET to detect cytosine, a nanoFET to detect guanine, and a nanoFET to detect thymine and,
   a memristor network in electrical communication with the plurality of nanoFETS.

2. The analyte detection system of claim 1, further comprising a target DNA molecule bound to a bead, wherein the bead is disposed in the nanochannel.

3. The analyte detection system of claim 1, further comprising an exonuclease enzyme bound to a bead, wherein the bead is disposed in the nanochannel.

4. A DNA sequencing system comprising:
   a plurality of nucleic acid base detection components, wherein the plurality nucleic acid base
   detection components comprises at least four nano-field effect transistor (nanoFET) detectors functionalized with different
   nucleosides or protein nucleic acids, and the at least four detectors comprise a detector configured to detect adenine, a detector configured to detect cytosine, a detector configured to detect guanine, and a detector configured to detect thymine; and
   a memristor network in electrical communication with the plurality of detectors.

5. The DNA sequencing system of claim 4, wherein the memristor network comprises a memristor/transistor hybrid network.

* * * * *